United States Patent
Zerkle et al.

(10) Patent No.: US 9,913,645 B2
(45) Date of Patent: Mar. 13, 2018

(54) LOCKOUT FEATURE FOR MOVABLE CUTTING MEMBER OF SURGICAL INSTRUMENT

(71) Applicant: ETHICON LLC, Guaynabo, PR (US)

(72) Inventors: Jason E. Zerkle, Blanchester, OH (US); Douglas B. Hoffman, Harrison, OH (US); William J. White, West Chester, OH (US); Robert J. Simms, Liberty Township, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/439,309

(22) Filed: Feb. 22, 2017

(65) Prior Publication Data

US 2017/0209144 A1    Jul. 27, 2017

Related U.S. Application Data

(63) Continuation of application No. 13/780,082, filed on Feb. 28, 2013, now Pat. No. 9,717,497.

(51) Int. Cl.
*A61B 17/072* (2006.01)
*A61B 90/00* (2016.01)
(Continued)

(52) U.S. Cl.
CPC ........ *A61B 17/07207* (2013.01); *A61B 90/03* (2016.02); *A61B 34/30* (2016.02);
(Continued)

(58) Field of Classification Search
USPC ...................................................... 227/175.4
See application file for complete search history.

(56) References Cited

U.S. PATENT DOCUMENTS 4,805,823 A    2/1989  Rothfuss
5,156,315 A *  10/1992  Green ............... A61B 17/07207
                                                227/178.1
(Continued)

FOREIGN PATENT DOCUMENTS

EP    0 488 768        6/1992
SU       1333319 A2    8/1987
WO   WO 2012/0142872   10/2012

OTHER PUBLICATIONS

Chinese Office Action, Notification of the First Office Action, dated Feb. 28, 2017 for Application No. 2014800108866, 7 pgs.
(Continued)

*Primary Examiner* — Hemant M Desai
*Assistant Examiner* — Tanzim Imam
(74) *Attorney, Agent, or Firm* — Frost Brown Todd LLC

(57) ABSTRACT

An end effector for use with a surgical instrument includes a first jaw, a second jaw, a blade assembly, and a lockout assembly. The first jaw removably couples with a staple cartridge. The second jaw is movably coupled with the first jaw. The blade assembly translates relative to the first jaw and includes a first tab. The lockout assembly includes a resilient member that biases the blade assembly to a lockout position. The lockout assembly engages the first tab of the blade assembly in the lockout position to prevent the blade assembly from translating distally relative to the first jaw when a staple cartridge is absent from the first jaw or when a spent staple cartridge is disposed in the first jaw.

19 Claims, 29 Drawing Sheets

(51) Int. Cl.
*A61B 34/30* (2016.01)
*A61B 17/00* (2006.01)
*A61B 17/29* (2006.01)

(52) U.S. Cl.
CPC ............ *A61B 2017/0023* (2013.01); *A61B 2017/00398* (2013.01); *A61B 2017/00734* (2013.01); *A61B 2017/07278* (2013.01); *A61B 2017/07285* (2013.01); *A61B 2017/2927* (2013.01); *A61B 2090/034* (2016.02); *A61B 2090/0801* (2016.02); *A61B 2090/0811* (2016.02)

(56) References Cited

U.S. PATENT DOCUMENTS

| | | | |
|---|---|---|---|
| 5,275,323 A * | 1/1994 | Schulze | A61B 17/07207 227/176.1 |
| 5,307,976 A | 5/1994 | Olsen et al. | |
| 5,415,334 A | 5/1995 | Williamson, IV et al. | |
| 5,465,895 A | 11/1995 | Knodel et al. | |
| 5,487,500 A * | 1/1996 | Knodel | A61B 17/07207 227/176.1 |
| 5,597,107 A | 1/1997 | Knodel et al. | |
| 5,632,432 A | 5/1997 | Schulze et al. | |
| 5,653,373 A | 8/1997 | Green et al. | |
| 5,662,258 A | 9/1997 | Knodel et al. | |
| 5,662,667 A | 9/1997 | Knodel | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 5,878,938 A | 3/1999 | Bittner et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,905,057 B2 | 6/2005 | Swayze et al. | |
| 6,959,852 B2 | 11/2005 | Shelton, IV et al. | |
| 6,978,921 B2 | 12/2005 | Shelton, IV et al. | |
| 6,988,649 B2 | 1/2006 | Shelton, IV et al. | |
| 7,000,818 B2 | 2/2006 | Shelton, IV et al. | |
| 7,044,352 B2 | 5/2006 | Shelton, IV et al. | |
| 7,083,075 B2 | 8/2006 | Swayze et al. | |
| 7,143,923 B2 | 12/2006 | Shelton, IV et al. | |
| 7,143,926 B2 | 12/2006 | Shelton, IV et al. | |
| 7,303,108 B2 | 12/2007 | Shelton, IV et al. | |
| 7,364,061 B2 | 4/2008 | Swayze et al. | |
| 7,367,485 B2 | 5/2008 | Shelton, IV et al. | |
| 7,380,696 B2 | 6/2008 | Shelton, IV et al. | |
| 7,404,508 B2 | 7/2008 | Smith et al. | |
| 7,419,080 B2 | 9/2008 | Smith et al. | |
| 7,434,715 B2 | 10/2008 | Shelton, IV et al. | |
| 7,455,208 B2 | 11/2008 | Wales et al. | |
| 7,490,749 B2 | 2/2009 | Schall et al. | |
| 7,524,320 B2 | 4/2009 | Tierney et al. | |
| 7,549,564 B2 | 6/2009 | Boudreaux | |
| 7,644,848 B2 | 1/2010 | Swayze et al. | |
| 7,658,311 B2 | 2/2010 | Boudreaux | |
| 7,691,098 B2 | 4/2010 | Wallace et al. | |
| 7,721,930 B2 | 5/2010 | McKenna et al. | |
| 7,753,245 B2 | 7/2010 | Boudreaux et al. | |
| 7,798,386 B2 | 9/2010 | Schall et al. | |
| 7,806,891 B2 | 10/2010 | Nowlin et al. | |
| 7,954,684 B2 | 6/2011 | Boudreaux | |
| 8,152,041 B2 | 4/2012 | Kostrzewski | |
| 8,210,411 B2 | 7/2012 | Yates et al. | |
| 8,245,898 B2 | 8/2012 | Smith et al. | |
| 8,408,439 B2 | 4/2013 | Huang et al. | |
| 8,453,914 B2 | 6/2013 | Laurent et al. | |
| 8,479,969 B2 | 7/2013 | Shelton, IV et al. | |
| 8,485,413 B2 | 7/2013 | Scheib et al. | |
| 8,573,461 B2 | 11/2013 | Shelton, IV et al. | |
| 8,573,465 B2 | 11/2013 | Shelton, IV | |
| 8,579,176 B2 | 11/2013 | Smith et al. | |
| 8,596,513 B2 | 12/2013 | Olson et al. | |
| 8,602,288 B2 | 12/2013 | Shelton, IV et al. | |
| 8,616,431 B2 | 12/2013 | Timm et al. | |
| 8,746,533 B2 | 6/2014 | Whitman et al. | |
| 8,783,541 B2 | 7/2014 | Shelton, IV et al. | |
| 8,800,838 B2 | 8/2014 | Shelton, IV et al. | |
| 8,820,605 B2 | 9/2014 | Shelton, IV et al. | |
| 8,844,789 B2 | 9/2014 | Shelton, IV et al. | |
| 9,186,142 B2 | 11/2015 | Fanelli et al. | |
| 9,301,759 B2 | 4/2016 | Spivey et al. | |
| 9,517,065 B2 | 12/2016 | Simms et al. | |
| 2005/0023324 A1* | 2/2005 | Doll | A61B 17/07207 227/175.2 |
| 2006/0180634 A1 | 8/2006 | Shelton, IV et al. | |
| 2007/0010838 A1 | 1/2007 | Shelton, IV et al. | |
| 2007/0073341 A1 | 3/2007 | Smith et al. | |
| 2007/0084897 A1 | 4/2007 | Shelton, IV et al. | |
| 2007/0175955 A1 | 8/2007 | Shelton, IV et al. | |
| 2011/0163147 A1* | 7/2011 | Laurent | A61B 17/072 227/175.2 |
| 2011/0290853 A1* | 12/2011 | Shelton, IV | A61B 17/07207 227/177.1 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239044 A1 | 8/2014 | Hoffman | |

OTHER PUBLICATIONS

Extended European Search Report and Written Opinion dated May 16, 2014 for Application No. EP 14157358, 10 pgs.
Extended European Search Report and Written Opinion dated Nov. 8, 2016 for Application No. EP 16176672.0, 8 pgs.
International Search Report dated May 27, 2014 for Application No. PCT/US2014/016202, 6 pgs.
International Preliminary Report on Patentability and Written Opinion dated Sep. 1, 2015 for Application No. PCT/US2014/016202, 9 pgs.
Russian Office Action and Search Report dated Nov. 23, 2017 for Application No. RU 2015140809, 8 pgs.

* cited by examiner

LOCKOUT FEATURE FOR MOVABLE CUTTING MEMBER OF SURGICAL INSTRUMENT

This application is a continuation of U.S. application Ser. No. 13/780,082, filed Feb. 28, 2013, published as U.S. Pat. Pub. No. 2014/0239041 on Aug. 28, 2014, entitled "Lockout Feature for Movable Cutting Member of Surgical Instrument," now U.S. Pat. No. 9,717,497, issued Aug. 1, 2017.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applies, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
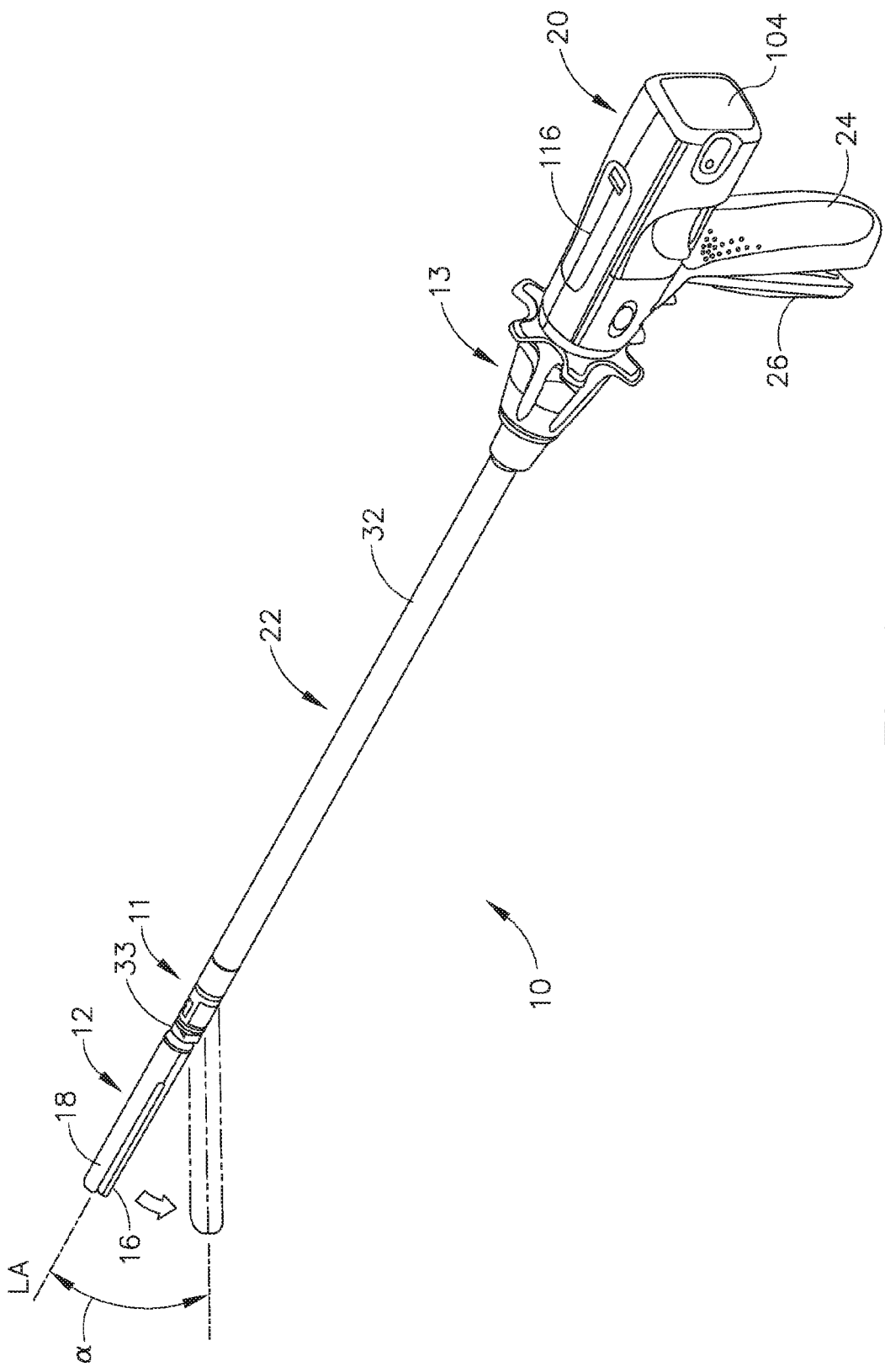
FIG. 1 depicts a perspective view of an exemplary articulating surgical stapling instrument.
Figure 2:
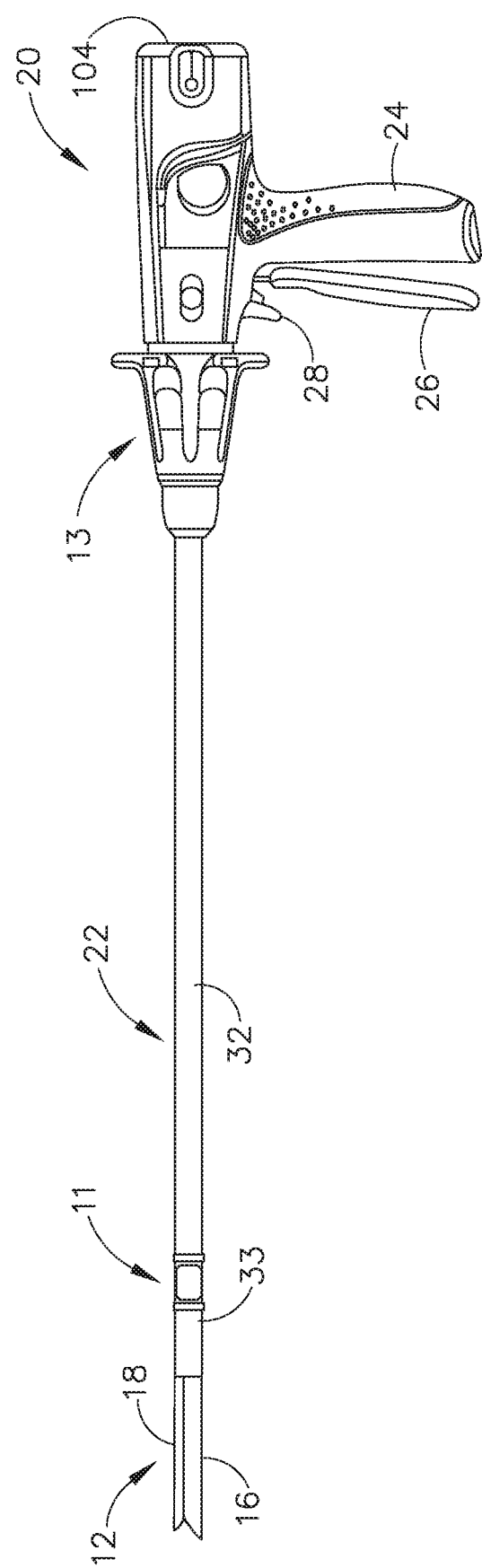
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion. (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. patent application Ser. No. 13/780,402, entitled "Surgical Instrument with Multi-Diameter Shaft," filed Feb. 28, 2013, published as U.S. Pat. Pub. No. 2014/0239038 on Aug. 28, 2014, now U.S. Pat. No. 9,795,379, issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. patent application Ser. No. 13/780,067, entitled "Surgical Instrument End Effector Articulation Drive with Pinion and Opposing Racks," filed Feb. 28, 2013, now U.S. Pat. No. 9,186,142, issued Nov. 17, 2015, the disclosure of which is incorporated by reference herein. Articulation joint (11) may also be constructed and operable in accordance with at least some of the teachings of U.S. patent application Ser. No. 13/780,402, published as U.S. Pat. Pub. No. 2014/0239038, on Aug. 28, 2014, now U.S. Pat. No. 9,795,379, issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. patent application Ser. No. 13/780,417, entitled "Installation Features for Surgical Instrument End Effector Cartridge," filed Feb. 28, 2013, published U.S. Pat. Pub. No. 2014/0239044 on Aug. 28, 2014, now U.S. Pat. No. 9,808,248, issued Nov. 7, 2017, the disclosure of which is incorporated by reference herein. Anvil (18) may be constructed in accordance with at least some of the teachings of U.S. patent application Ser. No. 13/780,106, entitled "Integrated Tissue Positioning and Jaw Alignment Features for Surgical Stapler," filed Feb. 28, 2013, now U.S. Pat. No. 9,517,065, issued Dec. 13, 2016, the disclosure of which is incorporated by reference herein; at least some of the teachings of U.S. patent application Ser. No. 13/780,120, entitled "Jaw Closure Feature for End Effector of Surgical Instrument," filed Feb. 28, 2013, published as U.S. Pat. Pub. No. 2014/0239036 on Aug. 28, 2014, now U.S. Pat. No. 9,839,421, issued Dec. 12, 2017, the disclosure of which is incorporated by reference herein; and/or at least some of the teachings of U.S. patent application Ser. No. 13/780,379, entitled "Staple Forming Features for Surgical Stapling Instrument," filed Feb. 28, 2013, published as U.S. Pat. Pub. No. 2014/0239037 on Aug. 28, 2014, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned, distal to articulation joint (11). Articulation joint (11) is operable to communicate/transmit longitudinal movement from closure tube (32) to closure ring (33).

Handle portion (20) also includes a firing trigger (28). An elongate member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower, aw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. Various exemplary alternative components, configurations, and operabilities for firing beam (14) are described in greater detail below. Other suitable forms that firing beam (14) may take will be apparent to those of ordinary skill in the art in view of the teachings herein.

Figure 3:
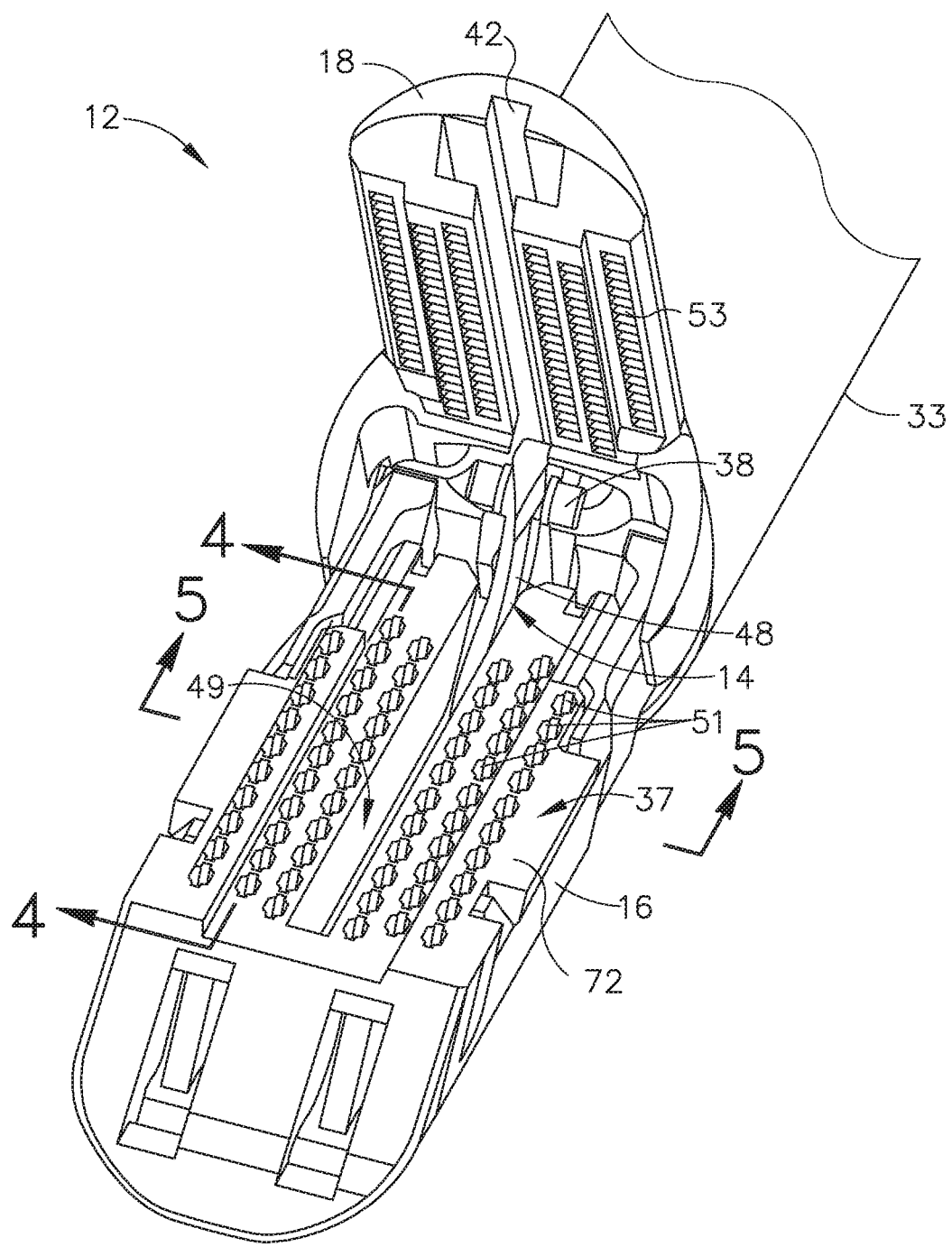
FIG. 3 depicts a perspective view of an opened end effector of the instrument of FIG. 1.
Figure 4A:
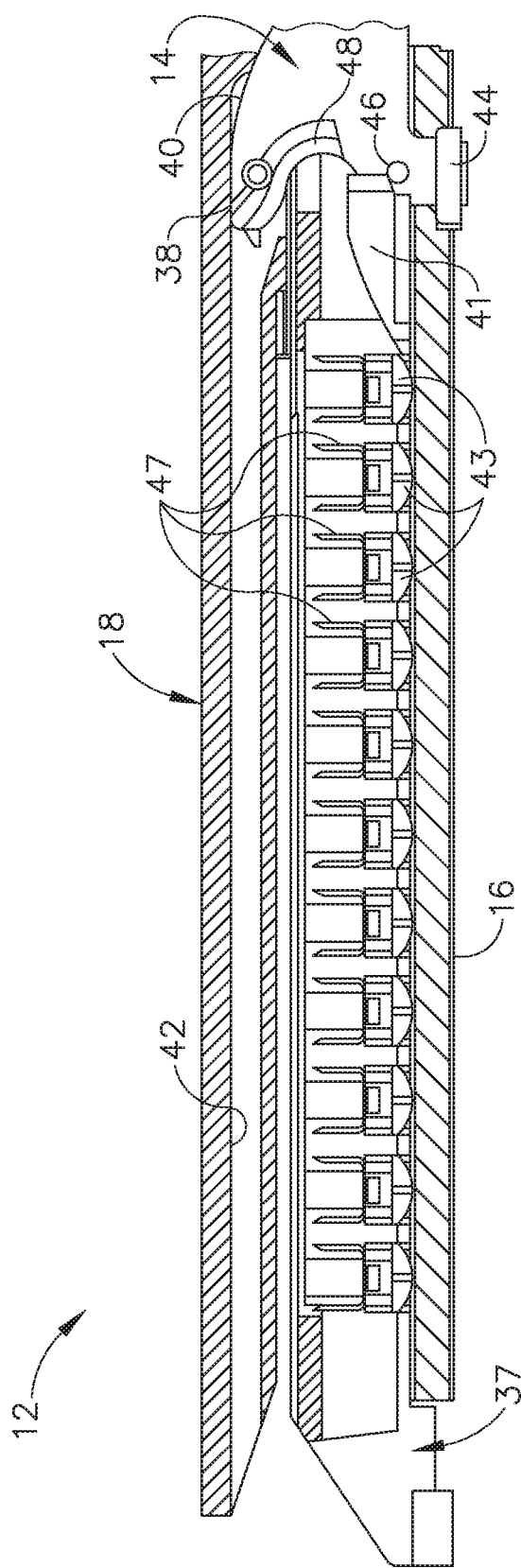
FIG. 4A depicts a side cross-sectional view of the end effector of FIG. 3, taken along line 4-4 of FIG. 3, with the firing beam in a proximal position.
Figure 4B:
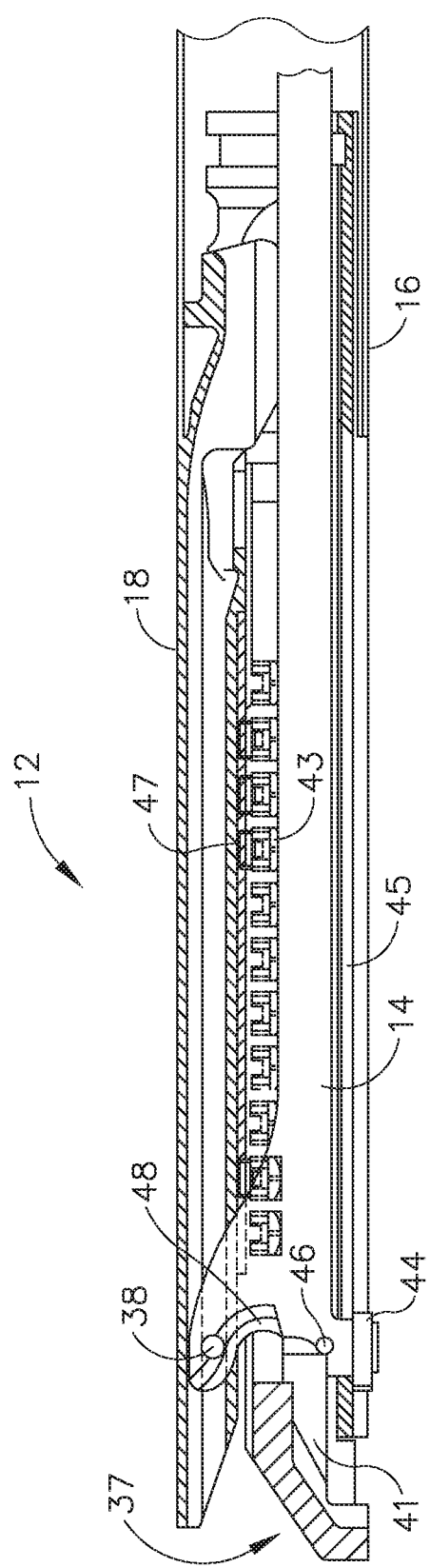
FIG. 4B depicts a side cross-sectional view of the end effector of FIG. 3, taken along line 4-4 of FIG. 3, with the firing beam in a distal position.
Figure 5:
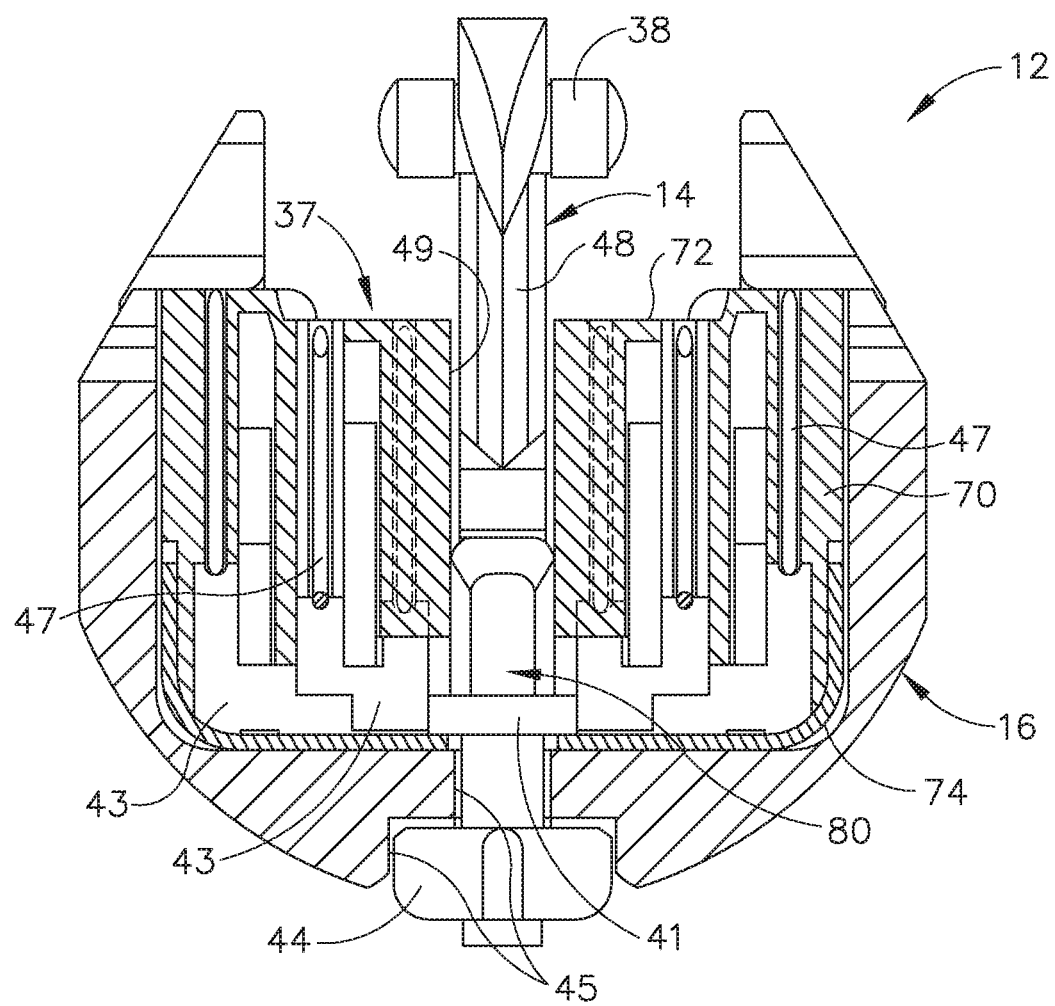
FIG. 5 depicts an end cross-sectional view of the end effector of FIG. 3, taken along line 5-5 of FIG. 3.
Figure 6:
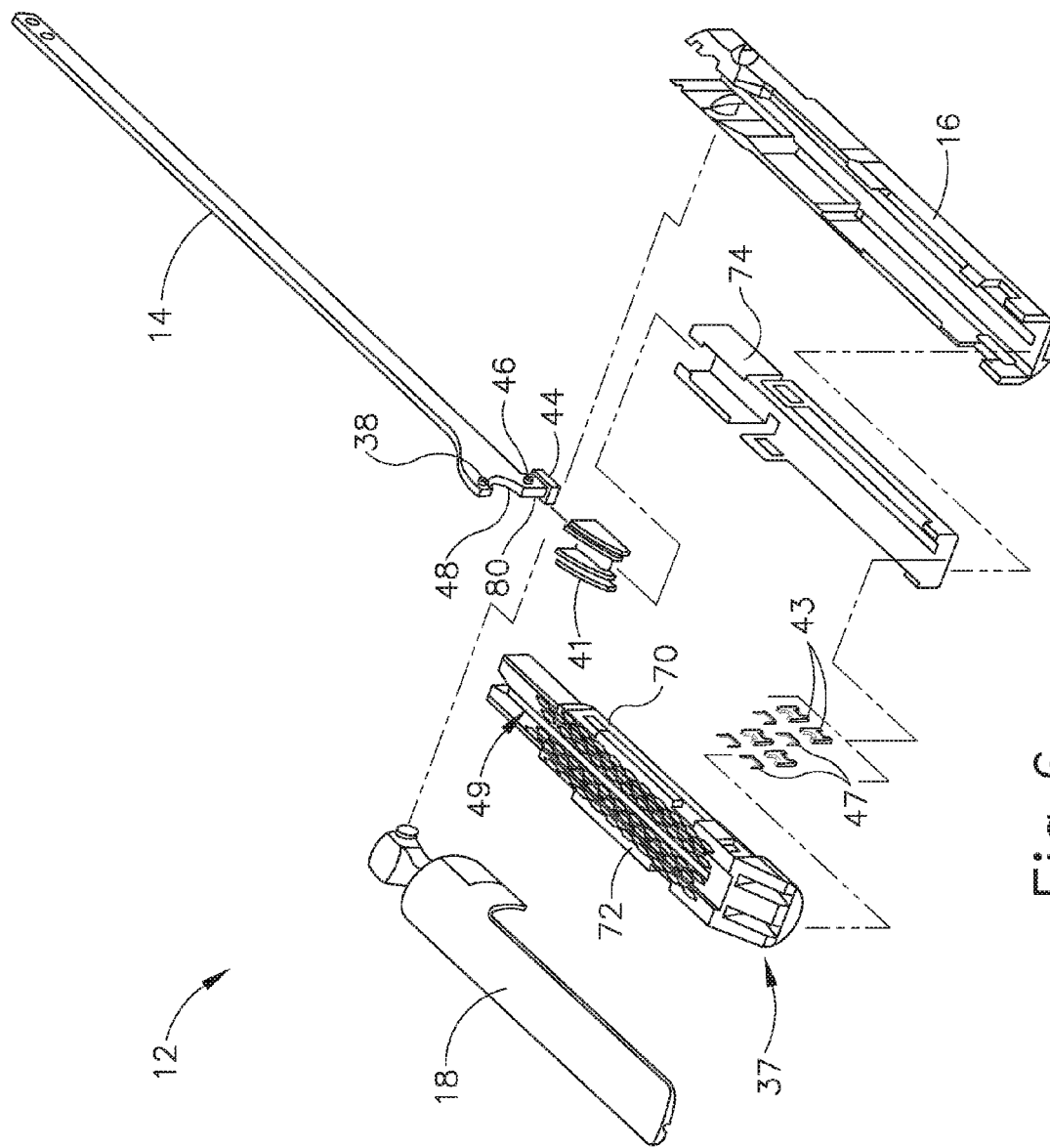
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. patent application Ser. No. 13/780,106, now U.S. Pat. No. 9,517,065, issued Dec. 13, 2016, the disclosure of which is incorporated by reference herein. In addition or in the alternative, staple cartridge (37) may be constructed and operable in accordance with at least some of the teachings of U.S. patent application Ser. No. 13/780,417, now U.S. Pat. No. 9,808,248, issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward caroming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
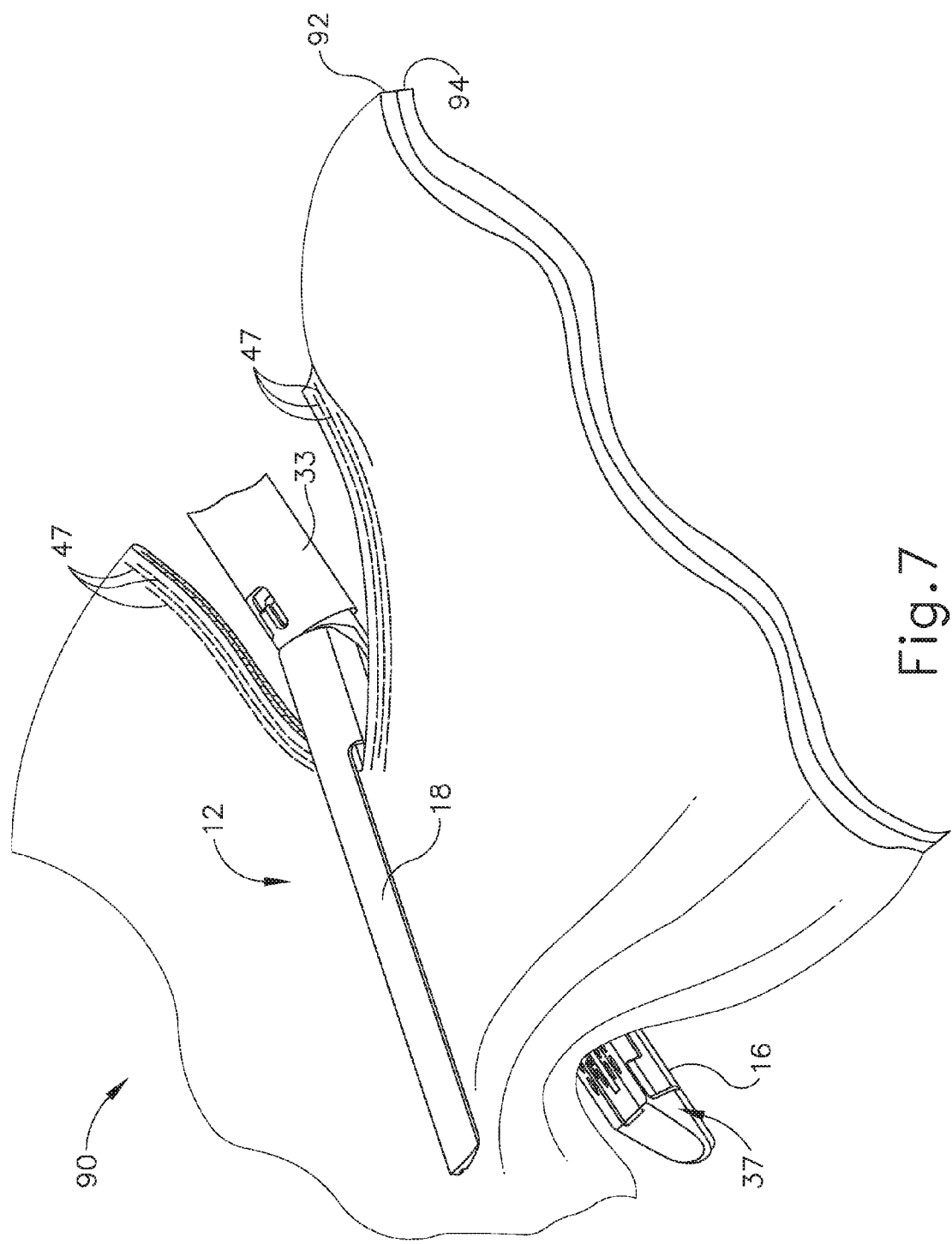
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; U.S. Pub. No. 2010/0264193, now U.S. Pat. No. 8,408,439; and/or 2012/0239012, now U.S. Pat. No. 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
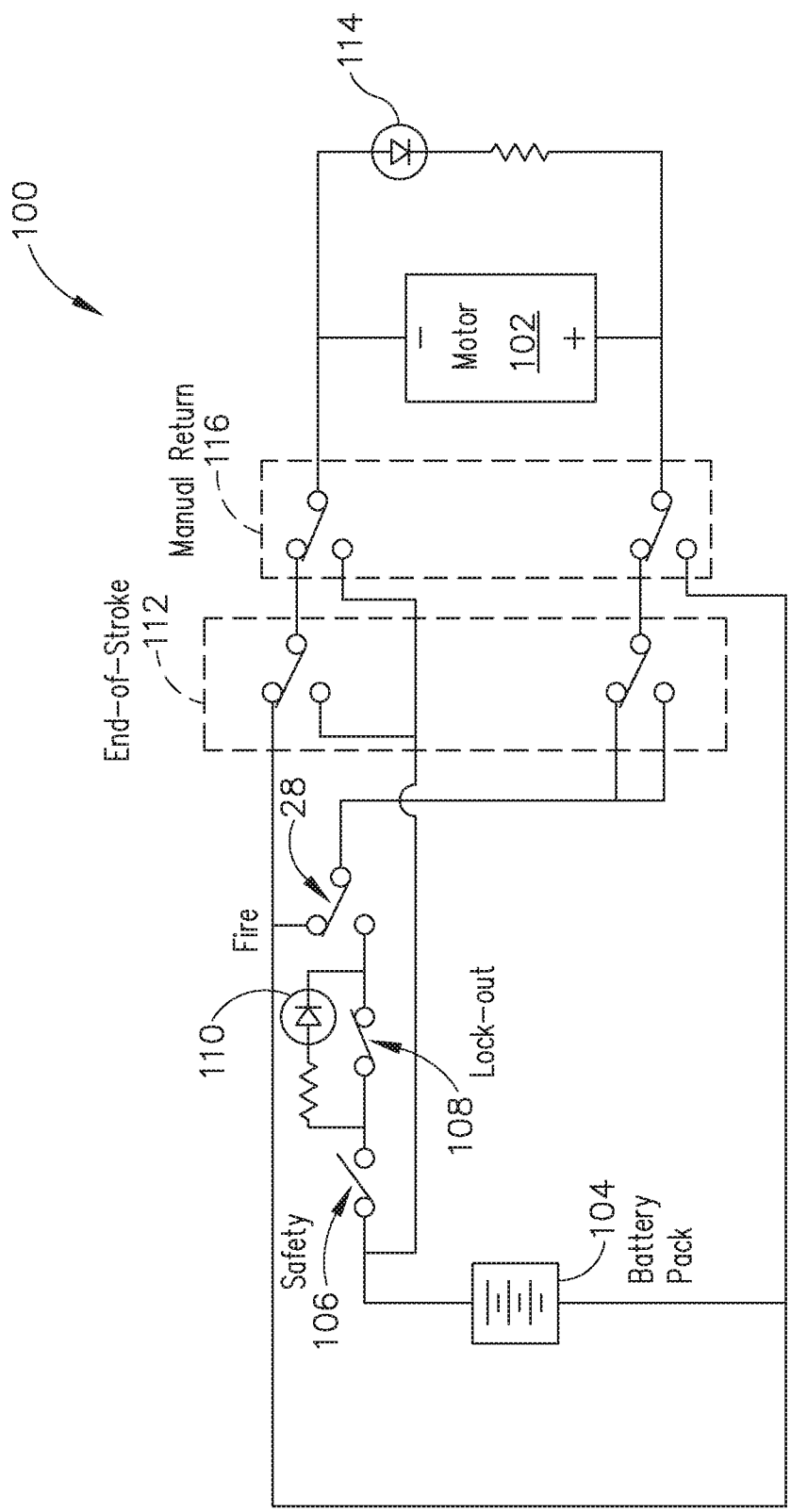
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
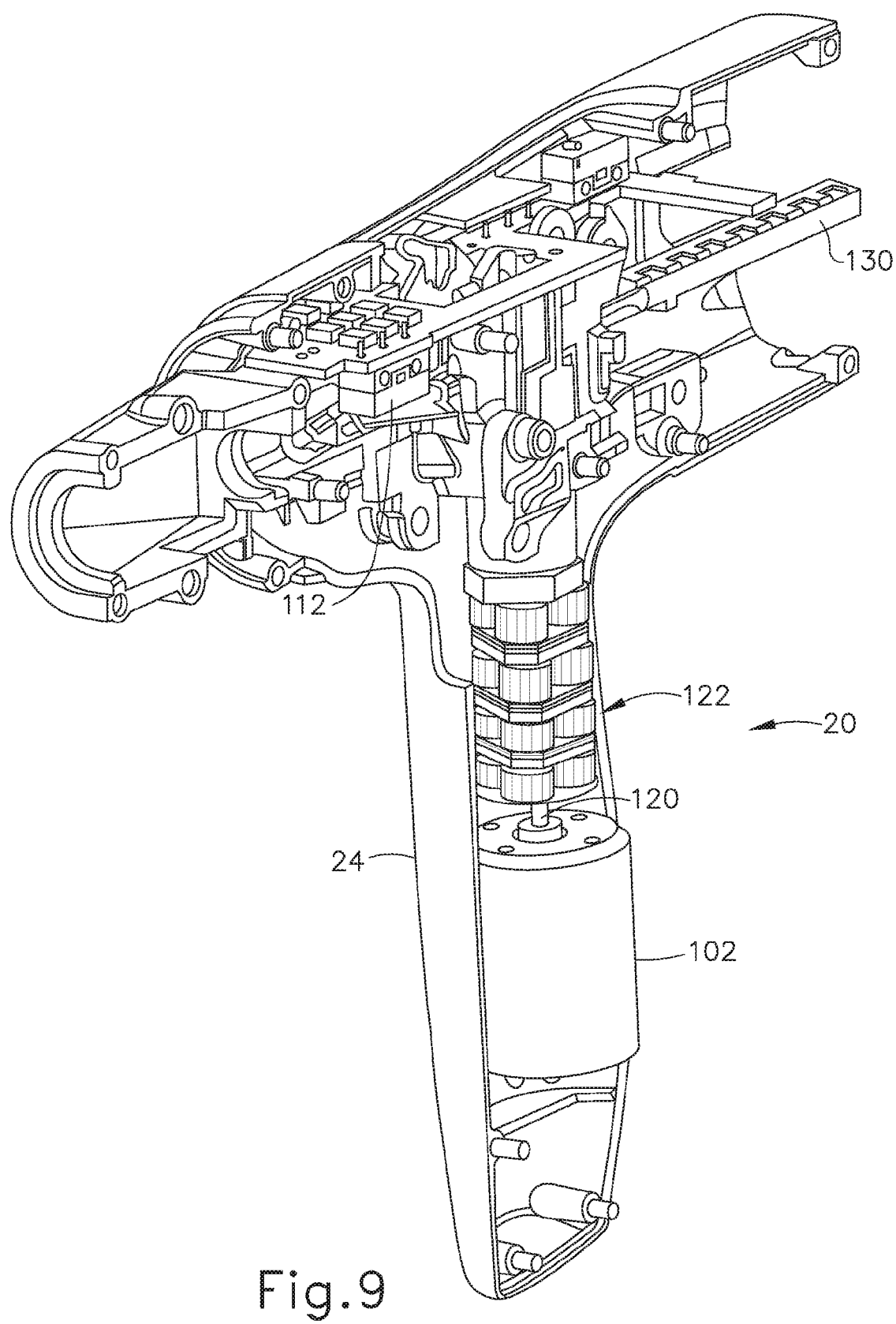
FIG. 9 depicts a perspective view of the handle assembly of the instrument of FIG. 1, with a housing half removed.
Figure 10:
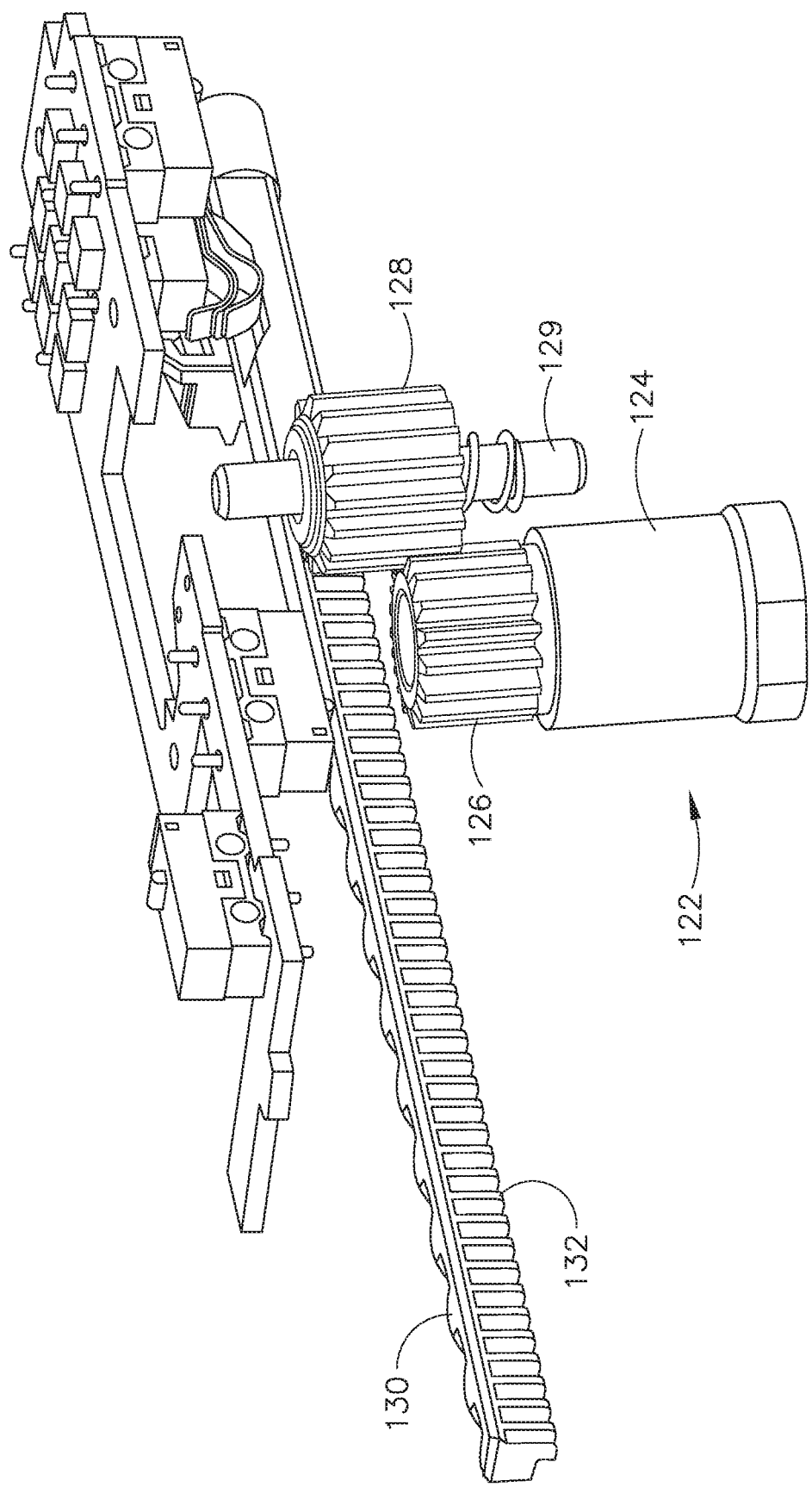
FIG. 10 depicts a perspective view of drive assembly components from the handle assembly of 9.
Figure 11:
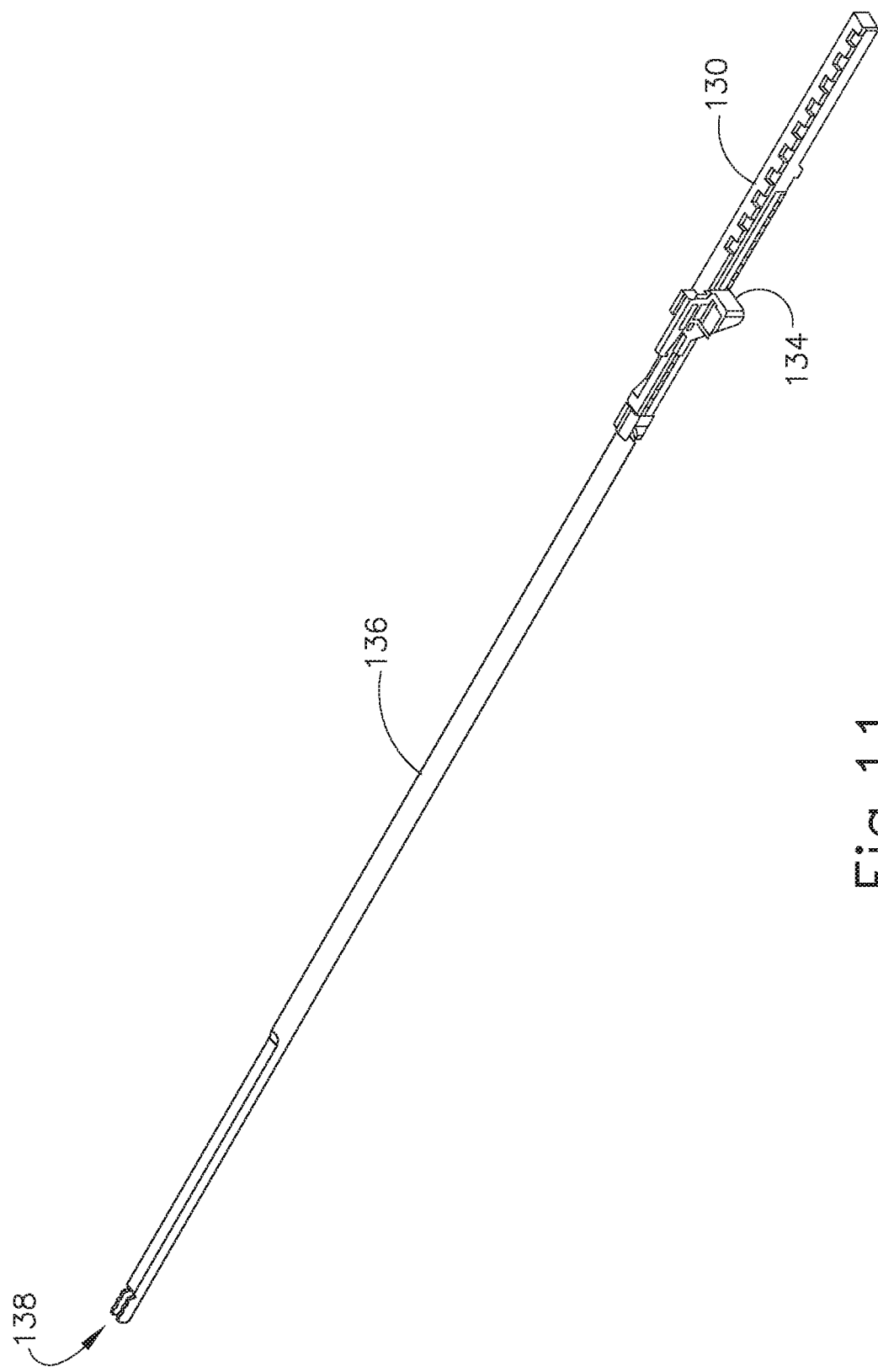
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14) within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012, now U.S. Pat. No. 8,453,914, the disclosure of which is incorporated by reference herein; and/or in accordance with at least some of the teachings of U.S. Pub. No. 2012/0239012, now U.S. Pat. No. 8,453,914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary End Effector Lockout Features

In some instances, it may be desirable to provide a lockout feature for end effector (12) to prevent inadvertent firing (i.e. distal advancement) of firing beam (14) and cutting edge (48) so that tissue positioned between jaws (216, 218) is not severed without being stapled. For example, it may be desirable to prevent firing beam (14) and cutting edge (48) from firing if a staple cartridge (37) has not been loaded within end effector (12) or after staples (47) have been driven from staple cartridge (37). Accordingly, lockout features may be provided within end effector (12) to prevent inadvertent firing of firing beam (14) and cutting edge (48). The examples below include several merely illustrative versions of lockout features that may be readily introduced to an end effector (12).

Figure 12:
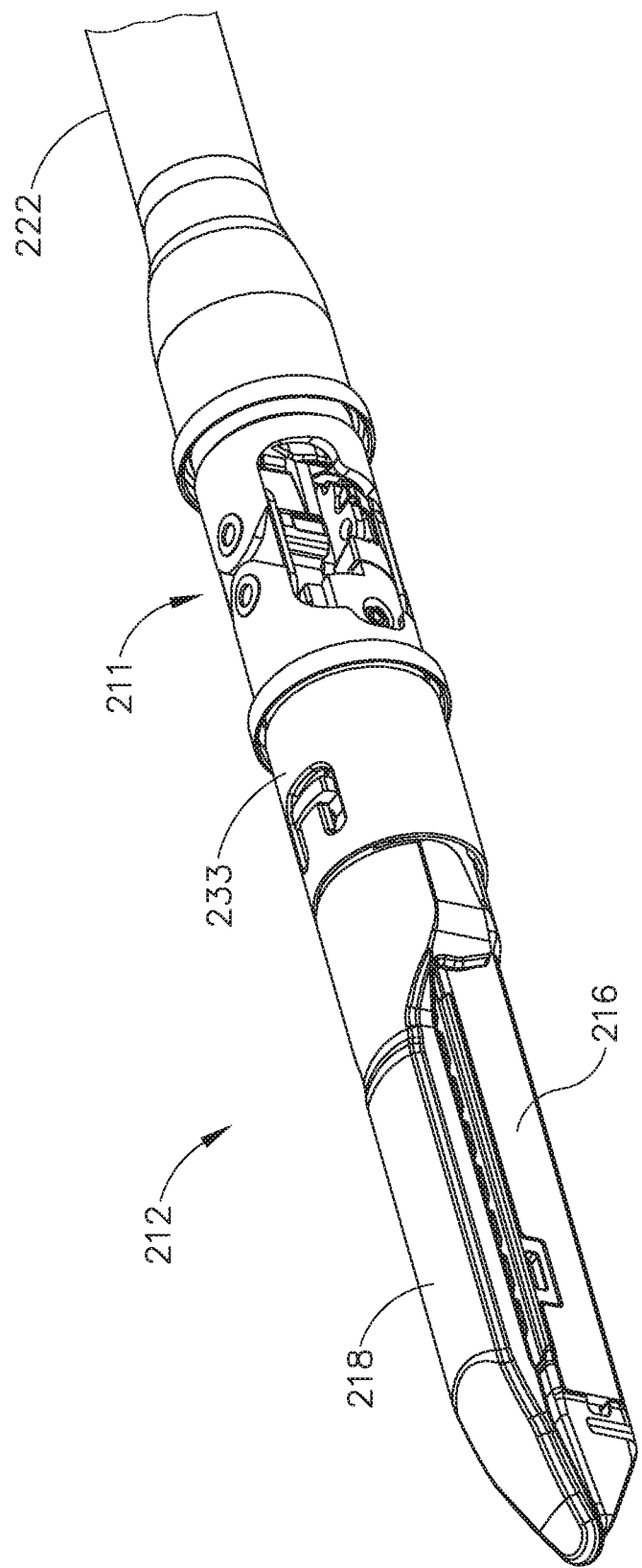
FIG. 12 depicts a perspective view of another exemplary end effector for use with the instrument of FIG. 1.
Figure 13:
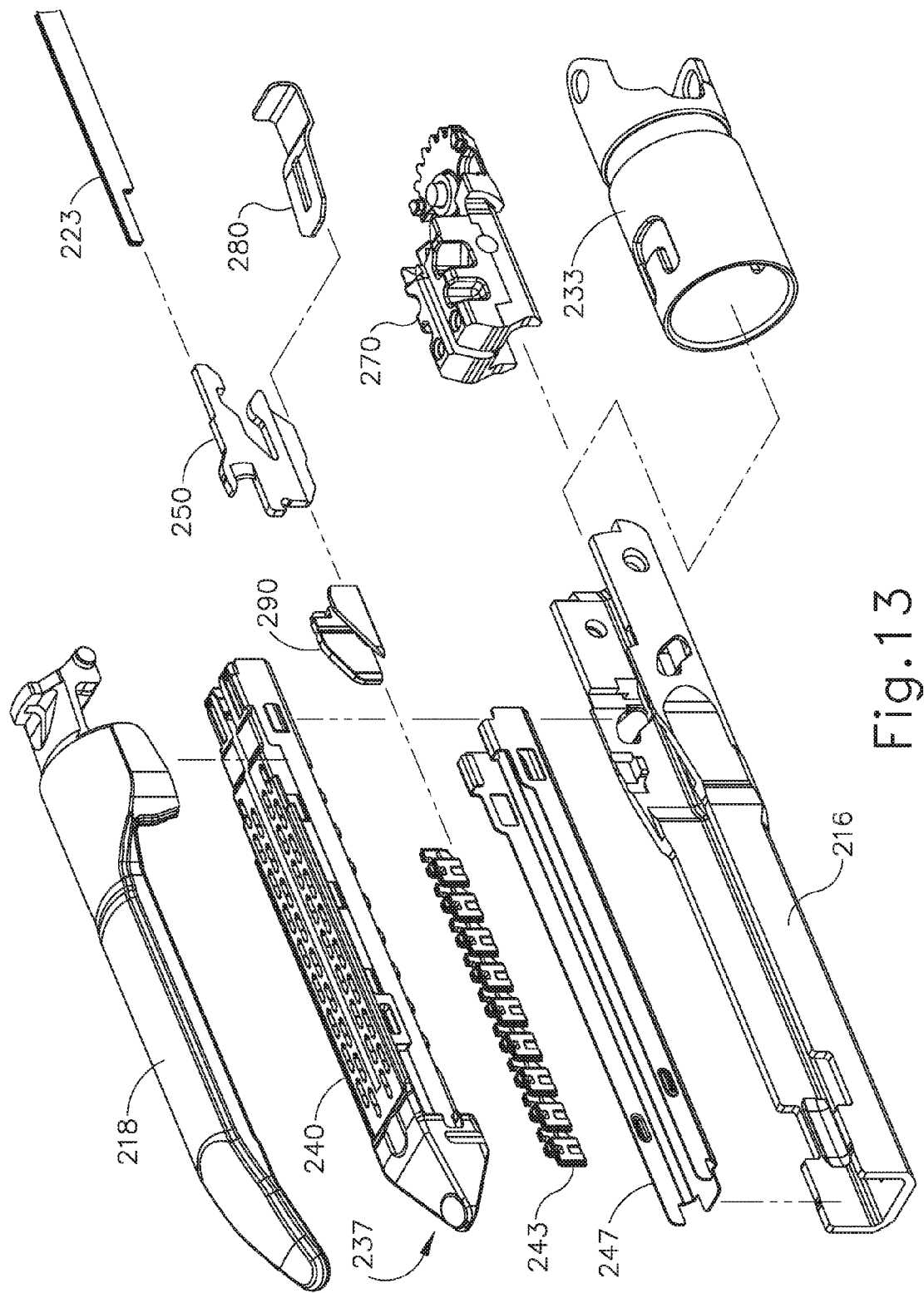
FIG. 13 depicts an exploded view of the end effector of FIG. 12.

FIGS. 12-13 show an exemplary end effector (212) that may be readily incorporated into instrument (10). End effector (212) comprises a lower jaw (216), a pivotable anvil (218), and a closure ring (233), which are similar to lower, jaw (16), anvil (18), and closure ring (33) of end effector (12). A staple cartridge (237) may be removably installed into a channel of lower jaw (216). Staple cartridge (237) of the present example is similar to staple cartridge (37) of end effector (12). As best seen in FIG. 13, staple cartridge (237) comprises a cartridge body (240) that is coupled with a lower cartridge tray (247). A wedge sled (290) and a plurality of staple drivers (243) are captured between cartridge body (240) and tray (247), with wedge sled (290) being located proximal to staple drivers (243). Although staples, similar to staples (47), have been omitted from FIG. 13 for clarity, it should be understood that staples (47) would be positioned directly above staple drivers (243). Wedge sled (290) and staple drivers (243) are similar to wedge sled (41) and staple drivers (243) of end effector (12) such that wedge sled (290) is configured to urge staple drivers (243) upwardly as wedge sled (290) is driven distally through staple cartridge (237) to drive staples (not shown in FIG. 13) vertically and into tissue positioned between jaws (216, 218). Wedge sled (290) of the present example is driven distally by blade assembly (250), which is positioned proximally of wedge sled (290). Beam (223) is coupled to blade assembly (250) (e.g., by welding). Beam (223) is similar to beam (14) and is configured to drive blade assembly (250) distally and/or proximally. Resilient member (280) is proximal of blade assembly (250) and is configured to removably engage blade assembly (250). Blade assembly (250) and resilient member (280) are positioned within frame member (270). Frame member (270) is positioned within closure ring (233) and coupled to a proximal end of lower jaw (216) such that frame member (270) couples with articulation joint (211) of shaft (222).

Articulation joint (211) and shaft (222) are similar to articulation joint (11) and shaft (22). By way of example only, articulation joint (211) and/or shaft (222) may be constructed in accordance with at least some of the teachings of U.S. patent application Ser. No. 13/780,067, now U.S. Pat. No. 9,186,142, issued Nov. 17, 2015, the disclosure of which is incorporated by reference herein; and/or U.S. patent application Ser. No. 13/780,402, now U.S. Pat. No. 9,795,379, issued Oct. 24, 2017, the disclosure of which is incorporated by reference herein. Alternatively, articulation joint (211) and/or shaft (222) may have any other suitable configurations.

Figure 14:
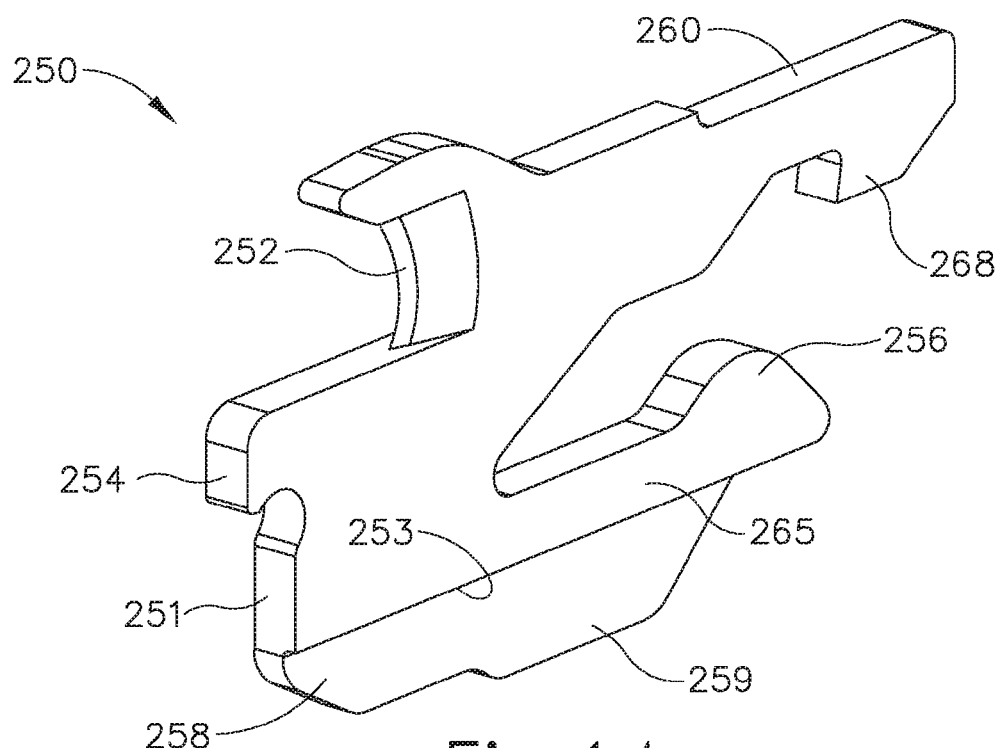
FIG. 14 depicts a perspective view of an exemplary blade of the end effector of FIG. 13.
Figure 15:
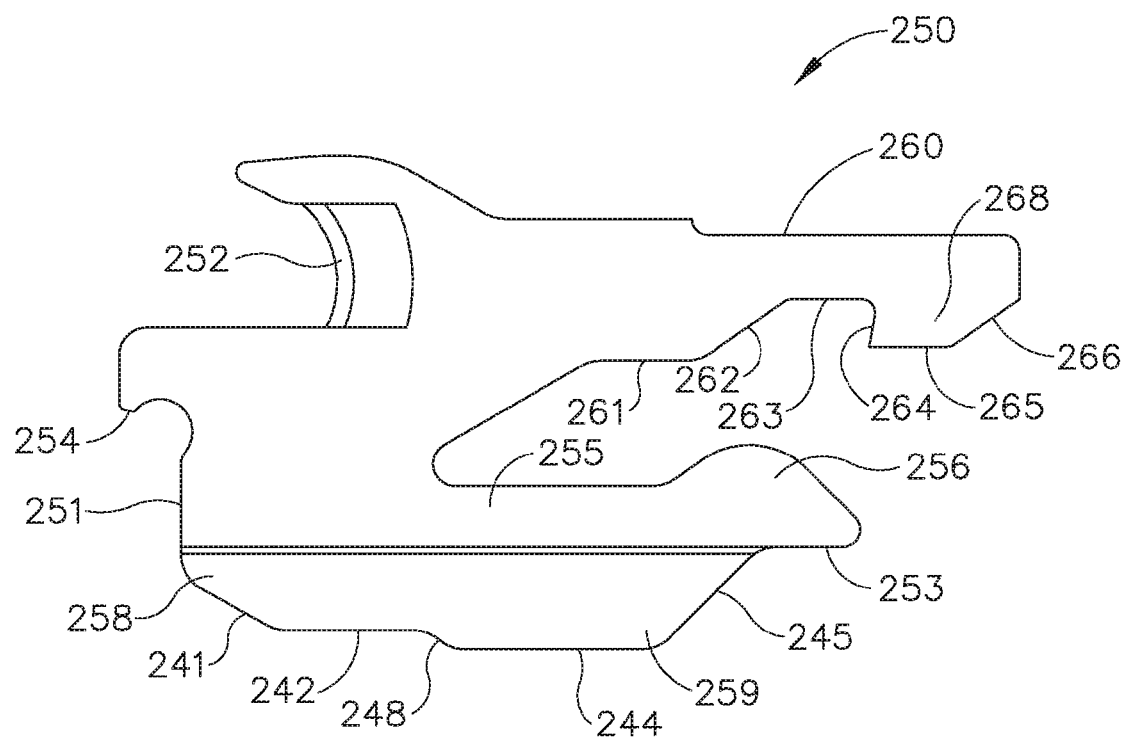
FIG. 15 depicts a side view of the blade of FIG. 14.

FIGS. 14-15 show blade assembly (250) in more detail. Blade assembly (250) comprises a cutting edge (252), an upper extension (260), and a lower extension (255). Cutting edge (252) is positioned on an upper distal portion of blade assembly (250) such that cutting edge (252) severs tissue as blade assembly (250) translates distally through lower jaw (216). Upper extension (260) extends proximally from cutting edge (252). Upper extension (260) comprises walls (261, 262, 263, 264, 265, 266) on a bottom surface of upper extension (260). Wall (261) extends proximally to wall (262). Wall (262) ramps upwardly to wall (263). Wall (263) extends proximally to wall (264), which extends downwardly to wall (265). Walls (262, 263, 264) together form a notch. Wall (265) extends proximally to wall (266), which ramps upwardly. Walls (264, 265, 266) form tab (268) that extends downwardly from upper extension (260). Tab (268) is configured to engage frame member (270) such that frame member (270) may prevent tab (268) and blade assembly (250) from advancing distally without a loaded staple cartridge (237), as will be described in greater detail below.

Lower extension (255) extends proximally from underneath cutting edge (252). A distal tip (254) and a distal wall (251) are positioned on a distal portion of lower extension (255). Distal tip (254) extends distally and downwardly from lower extension (255) such that distal tip (254) is configured to engage a top surface of wedge sled (290), as will be described in greater detail below. Distal wall (251) is vertically positioned on the distal portion of lower extension (255) beneath distal tip (254) such that distal wall (251) is configured to engage a proximal surface of wedge sled (290), as will also be described in greater detail below. Accordingly, distal tip (254) and distal wall (251) releasably engage wedge sled (290) when blade assembly (250) is translated distally within lower jaw (216) to thereby drive wedge sled (290) distally within lower jaw (216). A rounded tab (256) extends upwardly from a proximal portion of lower extension (255). Tab (256) is configured to engage resilient member (280) such that resilient member (280) may bias tab (256) and blade assembly (250) downwardly such that tab (268) of blade assembly (250) engages frame member (270) to prevent tab (268) and blade assembly (250) from advancing distally without a loaded staple cartridge (237).

A protrusion (258) extends downwardly from lower extension (255) and is configured to translate within a slot (214) of lower jaw (216). Protrusion (258) is not as wide as lower extension (255) such that a shelf (253) is formed between protrusion (258) and lower extension (255) on a bottom surface of lower extension (255). Accordingly, shelf (253) retains blade assembly (250) in a vertical position within slot (214) of lower jaw (216). Shelf (253) creates a retention method without the need for added or extended portions beyond the overall thickness of blade assembly (250). Protrusion (258) comprises a ramped wall (241) sloping toward wall (242). Wall (242) extends proximally to wall (248), which ramps downwardly to wall (244). Wall (244) extends proximally to wall (245) that ramps upwardly to lower extension (255). Walls (248, 244, 245) form tab (259) that extends downwardly from protrusion (258).

Figure 16:
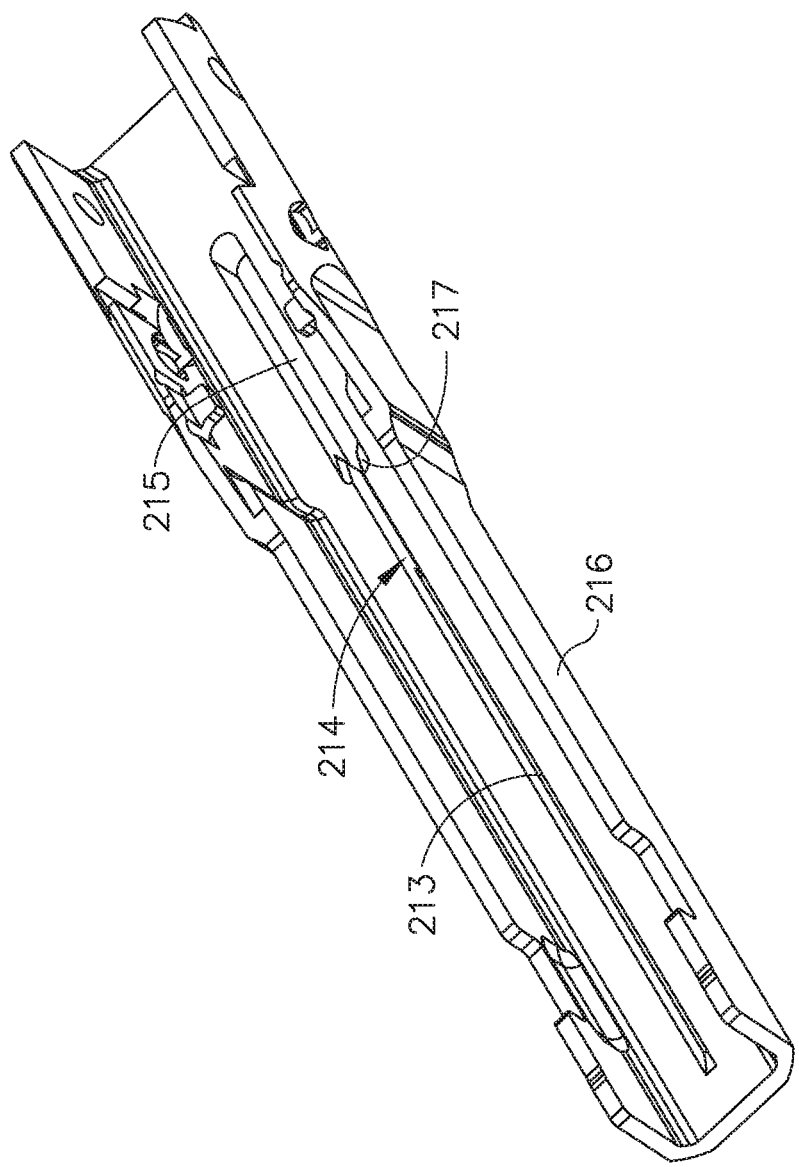
FIG. 16 depicts a perspective view of an exemplary stationary jaw of the end effector of FIG. 13.
Figure 17:
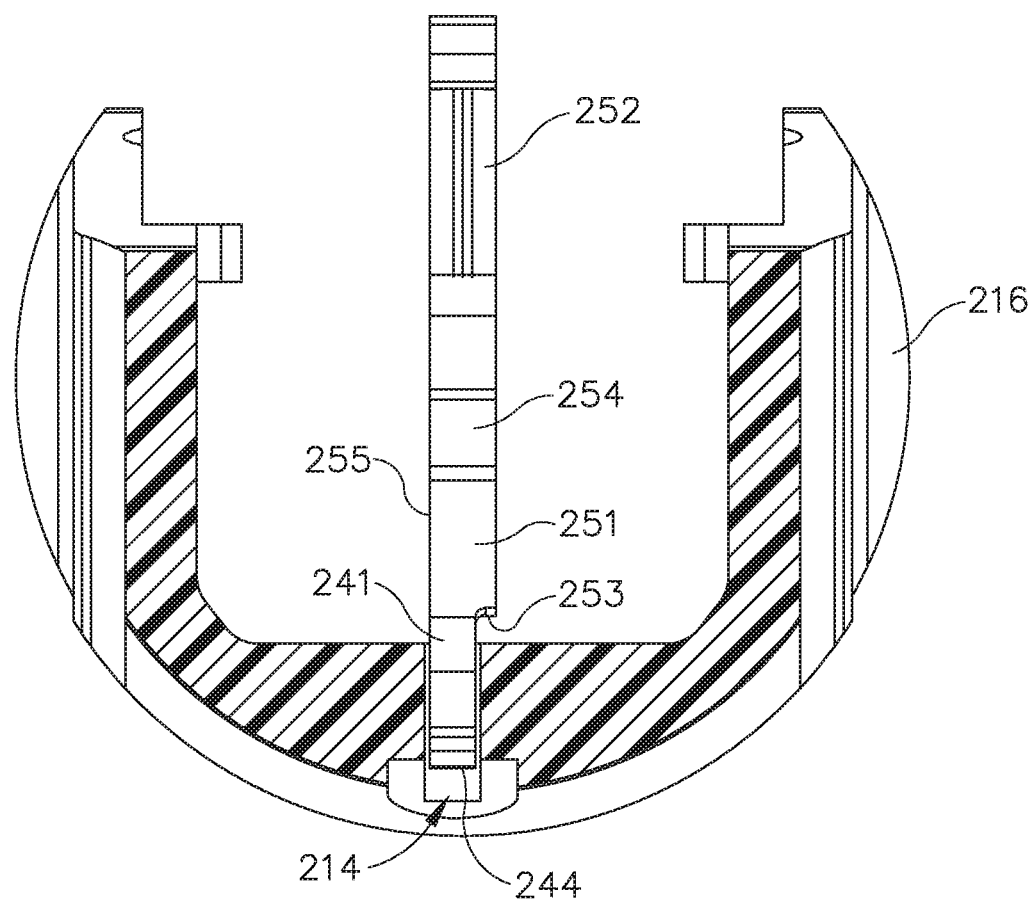
FIG. 17 depicts an end view of the blade of FIG. 14 positioned in a slot of the stationary jaw of FIG. 16.

As described above, blade assembly (250) is configured to translate proximally a or distally within lower jaw (216), based on the actuation of firing trigger (28) to drive motor (102) and firing beam (223). As shown in FIG. 16, lower jaw (216) comprises a slot (214) with a proximal portion (215) and a distal portion (213). Proximal portion (215) is wider than distal portion (213). Proximal portion (215) transitions to distal portion (213) via camming surface (217). FIG. 17 shows blade assembly (250) positioned within slot (214) of lower jaw (216) when blade assembly (250) is at a proximal, unfired position. Slot (214) receives protrusion (258) of blade assembly (250) such that protrusion (258) translates within slot (214) of lower jaw (216). Lower extension (255) is positioned above slot (214). Distal portion (213) of slot (214) has a lateral width sized to correspond to the lateral width of protrusion (258) such that shelf (253) extends laterally past distal portion (213) of slot (214) to maintain the vertical alignment or position of blade assembly (250) when blade assembly (250) is positioned within distal portion (213) of slot (214). Proximal portion (215) of slot (214) has a lateral width sized to correspond to the lateral width of lower extension (255) of blade assembly (250) such that protrusion (258) and lower extension (255) may fall within proximal portion (215) of slot (214) if blade assembly (250) is advanced without a loaded staple cartridge (237).

Figure 22:
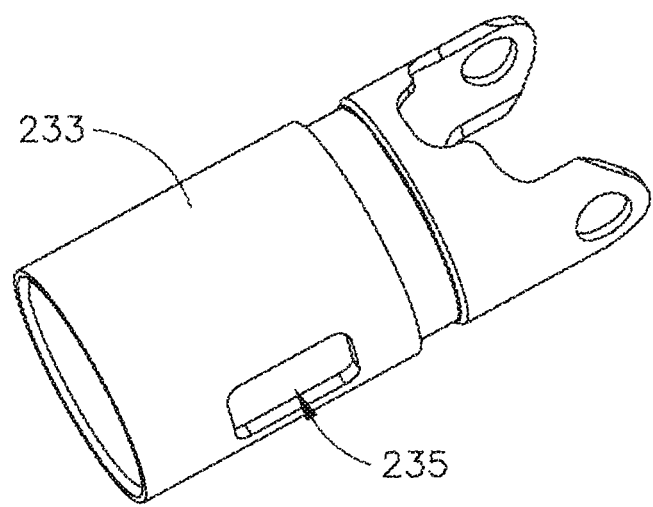
FIG. 22 depicts a perspective view of an exemplary closure ring of the end effector of FIG. 13.

Slot (214) extends continuously within lower jaw (216) to allow for the visualization of the position of blade assembly (250) within lower jaw (216) as blade assembly (250) translates proximally and/or distally. Closure ring (233) is coupled to lower jaw (216) to further allow for visualization of blade assembly (250). In the present example, closure ring (233) comprises an opening (235), as shown in FIG. 22. Closure ring (233) is slidably coupled with lower jaw (216) such that opening (235) is adjacent to proximal portion (215) of slot (214) when closure ring (233) is advanced to a distal position to close anvil (218) against lower jaw (216). Opening (235) is sized to correspond to tab (259) of blade assembly (250) such that closure ring (233) allows for visualization of tab (259) if protrusion (258) and lower extension (255) fall within proximal portion (215) of slot (214).

Figure 18:
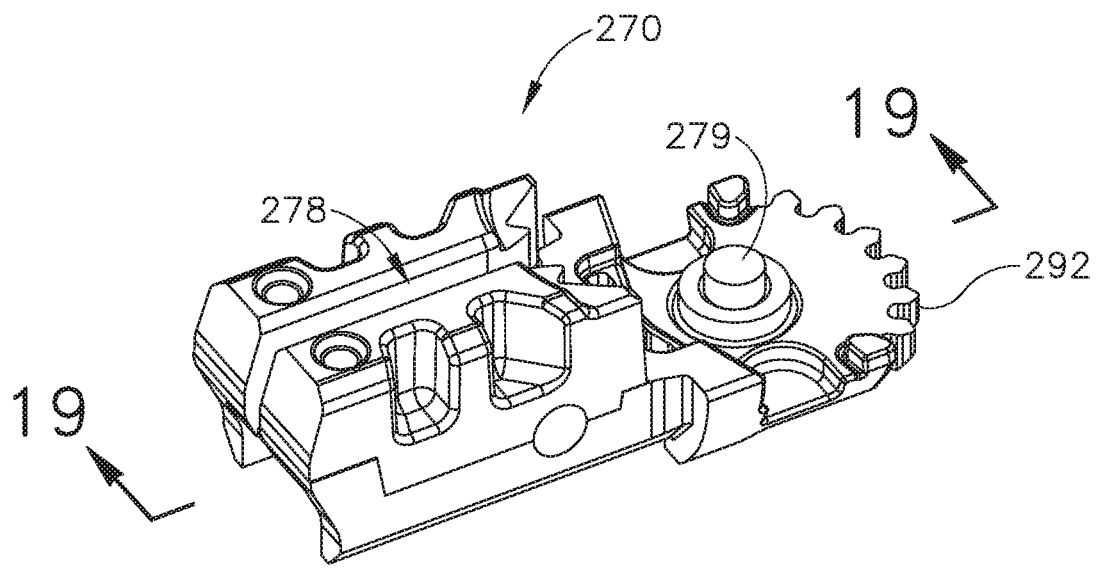
FIG. 18 depicts a perspective view of an exemplary lockout feature of the end effector of FIG. 13.
Figure 19:
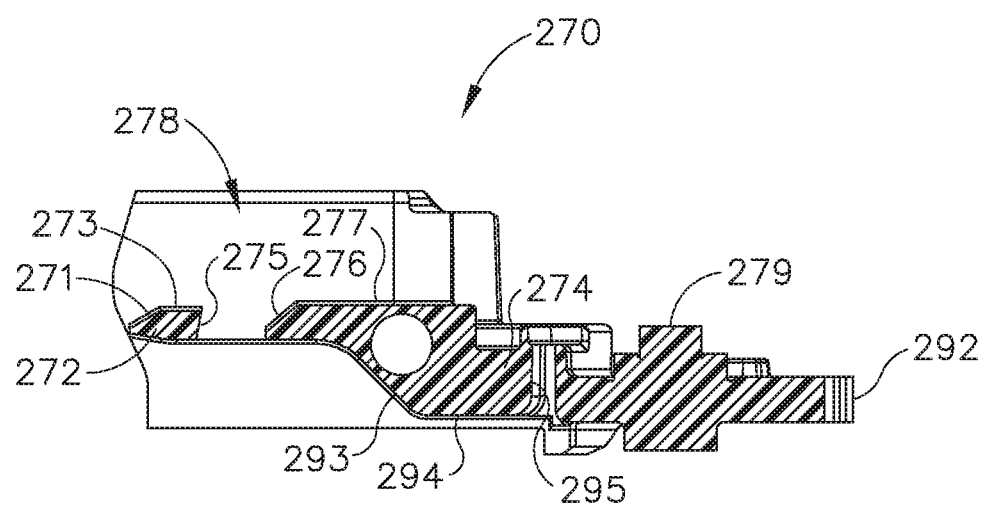
FIG. 19 depicts a cross sectional view of the lockout of feature of FIG. 18 taken along line 19-19 of FIG. 18.
Figure 23A:
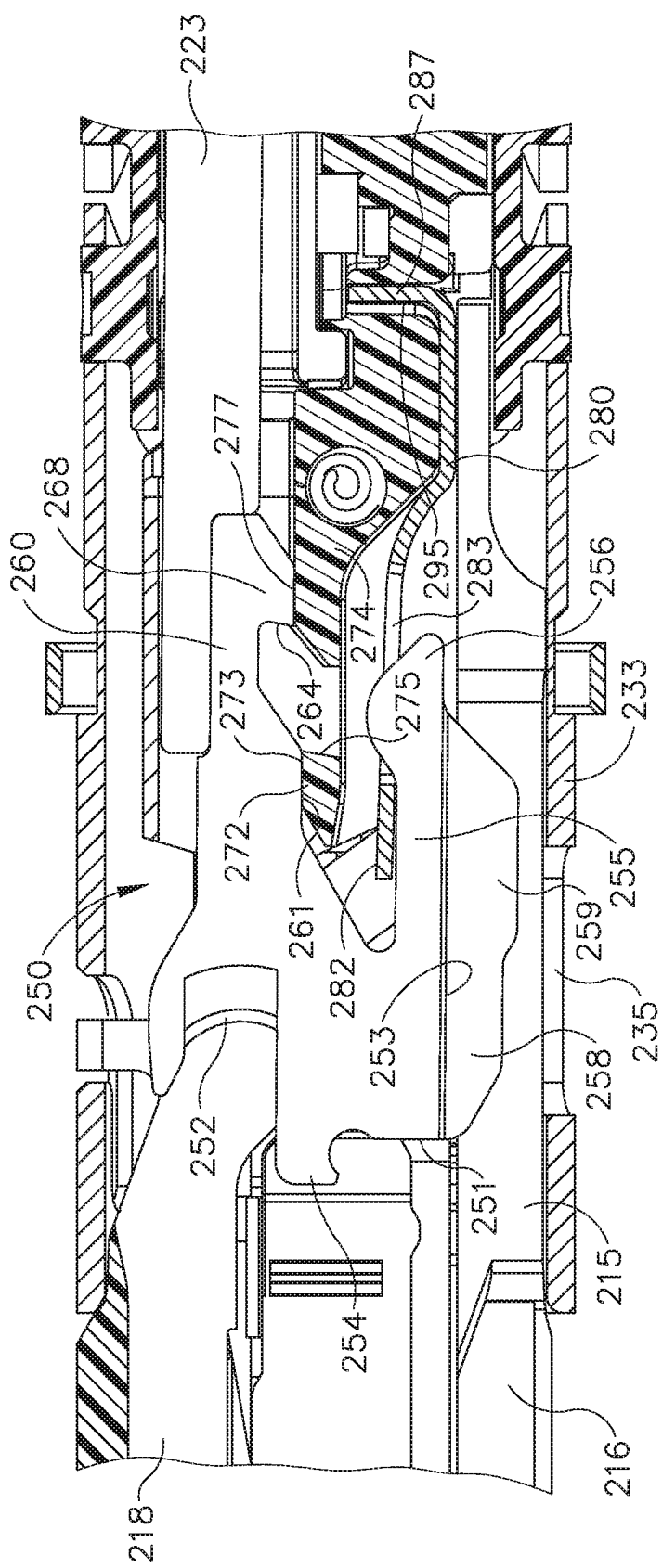
FIG. 23A depicts a side cross sectional view of the end effector of FIG. 13 in an initial position.

The proximal end of lower jaw (216) is coupled with frame member (270), shown in FIGS. 18-19. Frame member (270) comprises a channel (278), a pivot (279), and gear (292). A first engagement feature (272) and a second engagement feature (274) are positioned within channel (278), as shown in FIG. 19. Engagement features (272, 274) are configured to engage upper extension (260) of blade assembly (250). First engagement feature (272) comprises a wall (275) extending upwardly within channel (278). Wall (275) transitions to wall (273), which extends distally to wall (271). Wall (271) slopes downwardly in the distal direction. Second engagement feature (274) is proximal to first engagement feature (272). The top surface of second engagement feature (274) comprises a wall (277) extending distally to wall (276), which slopes downwardly in the distal direction. The bottom surface of second engagement feature (274) comprises a wall (293) sloping downwardly in the proximal direction to wall (294). Wall (294) extends proximally to wall (295), which extends upwardly from wall (294). The bottom surface of second engagement feature (274) is configured to engage resilient member (280), as shown in FIG. 23A. Gear (292) has teeth and is proximal to engagement feature (274). Pivot (279) extends upwardly from gear (292). Pivot (279) and gear (292) are configured to rotatably couple with articulation joint (211) of shaft (222) to allow end effector (212) to pivot to a desired angle (α) relative to shaft (222). By way of example only, gear (292) and/or other features of articulation joint (211) may be constructed in accordance with at least some of the teachings of U.S. patent application Ser. No. 13/780,067, now U.S. Pat. No. 9,186,142, issued Nov. 17, 2015, the disclosure of which is incorporated by reference herein; and/or U.S. application Ser. No. 13/780,162, entitled "Surgical Instrument with Articulation Lock Having a Detenting Binary Spring," filed Feb. 28, 2013, published as U.S. Pat. Pub. No. 2014/0239040 on Aug. 28, 2014, now U.S. Pat. No. 9,867,615, issued Jan. 16, 2018, the disclosure of which is incorporated by reference herein.

Figure 20:
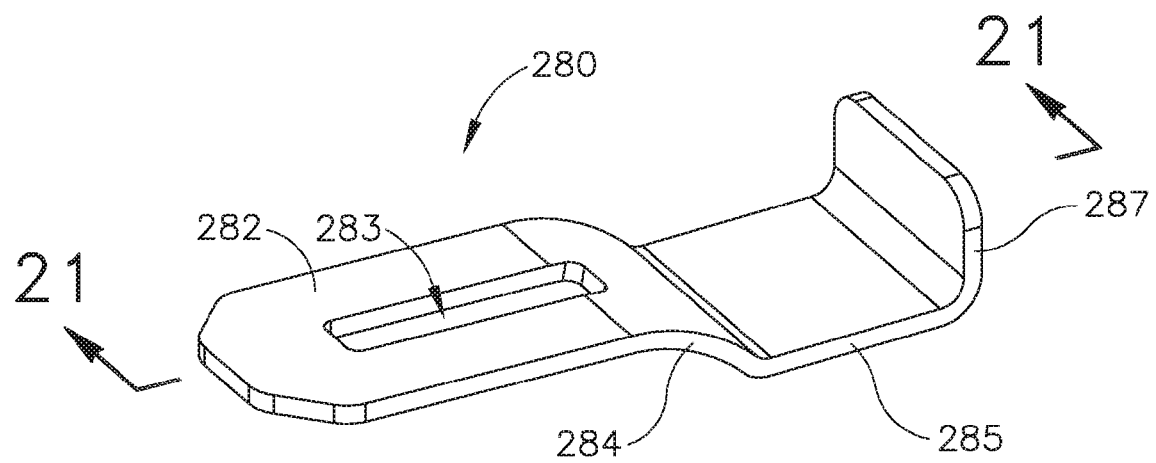
FIG. 20 depicts a perspective view of an exemplary spring of the end effector of FIG. 13.
Figure 21:
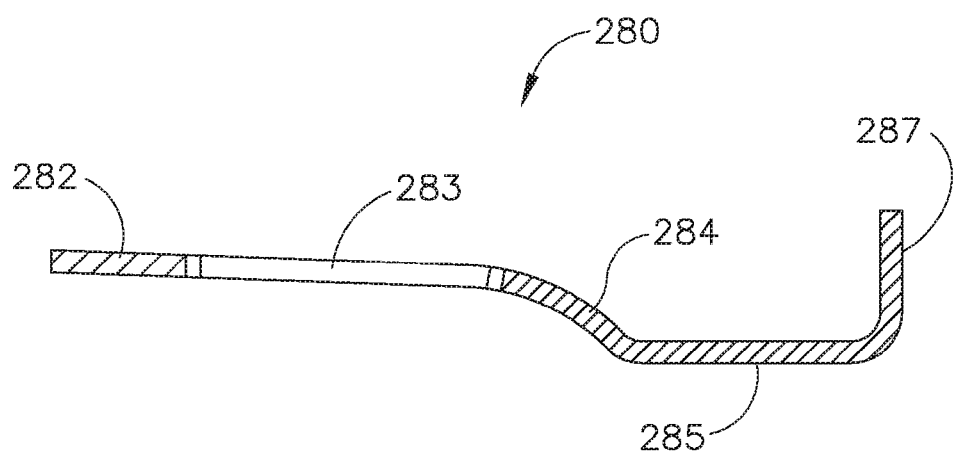
FIG. 21 depicts a cross sectional view of the spring of FIG. 20 taken along line 21-21 of FIG. 20.

FIGS. 20-21 show resilient member (280) in greater detail, Resilient member (280) comprises a distal portion (282) and a proximal portion (285). Distal portion (282) comprises an opening (283) that is configured to receive tab (256) of lower extension (255) of blade assembly (250). Distal portion (282) transitions to proximal portion (285) via ramped portion (284) that slopes downwardly in the proximal direction. Ramped portion (284) is compliant and is configured to resiliently bias distal portion (282) downwardly. A wall (287) extends upwardly from the proximal end of proximal portion (285). Wall (287) engages wall (295) of frame member (270) such that frame member (270) is configured to axially retain resilient member (280).

A. Exemplary Lockout Sequence

Figure 23B:
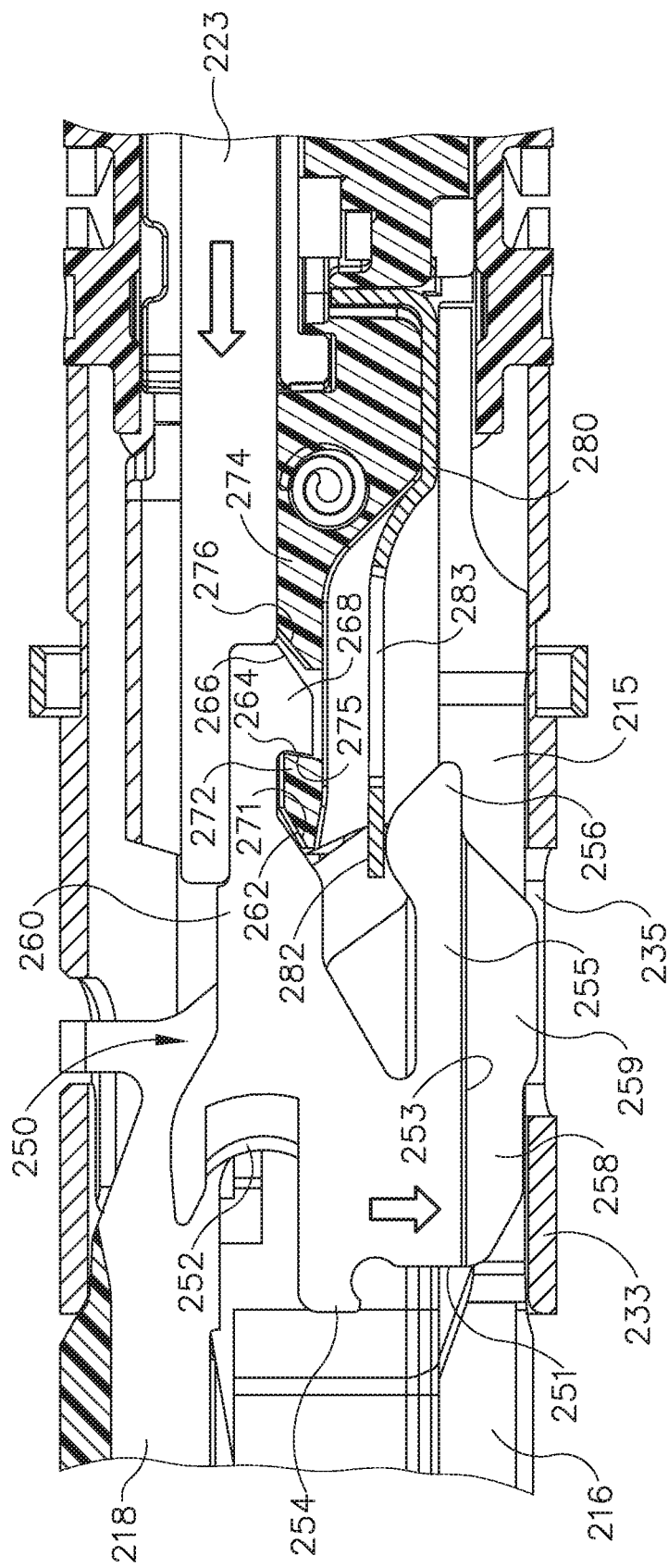
FIG. 23B depicts a side cross sectional view of the end effector of FIG. 13 in a lockout position.

FIGS. 23A-23B show an attempt at firing blade assembly (250) without a properly loaded staple cartridge (237). For instance, instrument (10) may be inserted to a surgical site in a nonarticulated state, with jaws (216, 218) closed. Once articulation joint (211) and end effector (212) are inserted to the desired site within the patient, anvil (218) may be pivoted away from lower jaw (216) to the open end effector (212) such that jaws (216, 218) may be positioned about tissue. Articulation joint (211) may be remotely articulated by articulation control (13), such that end effector (212) may be deflected to a desired angle (cm). Closure trigger (26) may then be actuated toward pistol grip (24) to cause the closing of anvil (218) toward lower jaw (216). Such closing of anvil is provided through a closure tube (32) and closure ring (233), which both longitudinally translate relative to handle portion (20) and lower jaw (216) in response to pivoting of closure trigger (26) relative to pistol grip (24). Articulation joint (211) is operable to communicate longitudinal movement from closure tube (32) to closure ring (233).

FIG. 23A shows end effector (212) in an initial position just after jaws (216, 218) are closed, but without a staple cartridge (237) in lower jaw (216). In the initial position, upper extension (260) of blade assembly (250) is positioned above engagement features (272, 274) of frame member (270). Wall (261) of upper extension (260) is resting on wall (273) of first engagement feature (272), while tab (268) of upper extension (260) is resting on wall (277) of second engagement feature (274). Resilient member (280) is positioned between lower jaw (216) and frame member (270). Wall (287) of resilient member (280) is engaged with wall (295) of frame member (270) such that wall (295) is configured to axially retain resilient member (280). Opening (283) of resilient member is positioned above lower extension (255) of blade assembly (250) such that tab (256) of lower extension (255) is positioned within opening (283) of resilient member (280). Protrusion (258) of lower extension (255) is positioned within proximal portion (215) of slot (214) of lower jaw (216). Protrusion (258) is vertically aligned within slot (214) such that shelf (253) is positioned above slot (214). Accordingly, blade assembly (250) is ready to be fired in from the initial position.

However, in the present example, a staple cartridge (237) was not properly loaded in end effector (212). Accordingly, distal tip (254) and distal wall (251) are not engaged with a sled (290). When firing trigger (28) is actuated to drive firing beam (223) and blade assembly (250) distally without a properly loaded staple cartridge (237), blade assembly (250) falls downwardly within end effector (212) to engage engagement features (272, 274) of frame member (270) to prevent blade assembly (250) from travelling further distally within lower jaw (216), as shown in FIG. 23B. As blade assembly (250) is pushed distally without a properly loaded staple cartridge (237), tab (256) of lower extension (255) of blade assembly (250) translates distally from opening (283) of resilient member (280). Tab (256) then engages distal portion (282) of resilient member (280). Because distal portion (282) of resilient member (280) is biased downwardly, resilient member (280) pushes tab (256) of blade assembly (250) downward. This causes tab (268) of upper extension (255) of blade assembly (250) to fall downwardly between engagement features (272, 274). Accordingly, wall (264) of tab (268) engages wall (275) of first engagement feature (272) to prevent blade assembly (250) from travelling any further distally to lock blade assembly (250) within end effector (212). It should be understood that the foregoing lockout may also occur when an operator intends to advance firing beam (233) from a proximal position to a distal position when a spent staple cartridge (237) is loaded in end effector. The lockout features thus prevent advancement of firing beam (233) when no staple cartridge (237) is loaded in end effector (212); and when a cartridge (237) that is in end effector (2112) has already been fired and firing beam (233) has been retracted back to a proximal position.

Figure 24A:
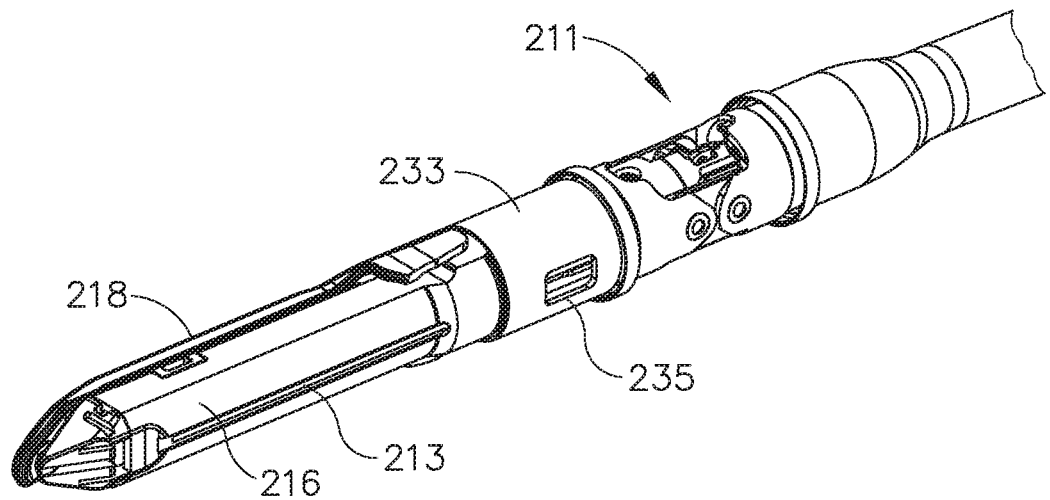
FIG. 24A depicts a bottom perspective view of the end effector of FIG. 13 in the initial position.
Figure 24B:
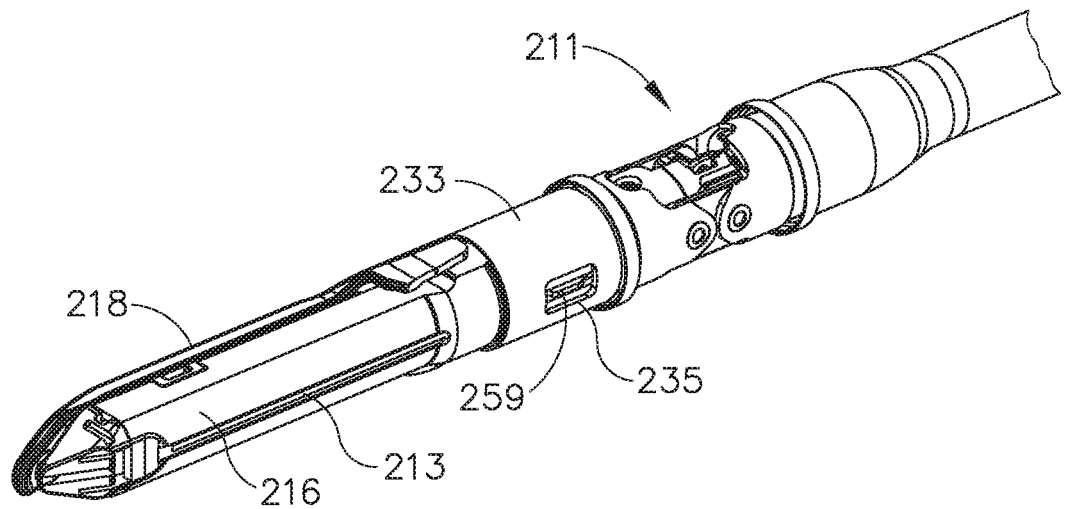
FIG. 24B depicts a bottom perspective view of the end effector of FIG. 13 in the lockout position.

As blade assembly (250) falls downwardly to the locked position shown in FIG. 23B, lower extension (255) and protrusion (258) of blade assembly fall within proximal portion (215) of slot (214) of lower jaw (216). Accordingly, tab (259) of protrusion (258) extends through proximal portion (215) of slot (214) and through opening (235) of closure ring (233). This provides a visual indication that blade assembly (250) is in the lockout position, as shown in FIGS. 24A-24B. In FIG. 24A, blade assembly (250) is in the initial position such that tab (259) is positioned within slot (214) above opening (235) of closure ring (233). When blade assembly (250) falls downwardly to the lockout position, as shown in FIG. 24B, tab (259) extends through opening (235) of closure ring (233) to provide a visual indication of lockout. By providing lockout features and visual indications within the space of closure ring (233), the overall length of articulation joint (211) may be minimized.

Blade assembly (250) may be returned to the initial position of FIG. 23A after blade assembly (250) is in the lockout position of FIG. 23B. For instance, motor (102) may be activated to pull beam (223) and blade assembly (250) proximally to return blade assembly (250) to the initial position of FIG. 23A. As blade assembly (250) translates proximally, ramped walls (262, 266) of upper extension (260) of blade assembly (250) slide proximally against ramped walls (271, 276) of engagement features (272, 274). As upper extension (260) translates proximally against engagement features (272, 274), walls (271, 276) of engagement features (272, 274) push upper extension (260) and blade assembly (250) upwardly through a caroming action. Tab (256) of blade assembly (250) also travels upwardly to again be positioned within opening (283) of resilient member (280). This returns blade assembly (250) to the initial position, as shown in FIG. 23A.

B. Exemplary Firing Sequence

FIGS. 25A-25F show blade assembly (250) being fired with a properly loaded staple cartridge (237). For instance, instrument (10) may be inserted to a surgical site in a nonarticulated state, with jaws (216, 218) closed. Once articulation joint (211) and end effector (212) are inserted to the desired site within the patient, anvil (218) may be pivoted away from lower jaw (216) to the open end effector (212) such that jaws (216, 218) may be positioned about tissue. Articulation joint (211) may be remotely articulated by articulation control (13), such that end effector (212) may be deflected to a desired angle (a). Closure trigger (26) may then be actuated toward pistol grip (24) to cause the closing of anvil (218) toward lower jaw (216). Such closing of anvil is provided through a closure tube (32) and closure ring (233), which both longitudinally translate relative to handle portion (20) and lower jaw (216) in response to pivoting of closure trigger (26) relative to pistol grip (24). Articulation joint (211) is operable to communicate longitudinal movement from closure tube (32) to closure ring (233).

Figure 25A:
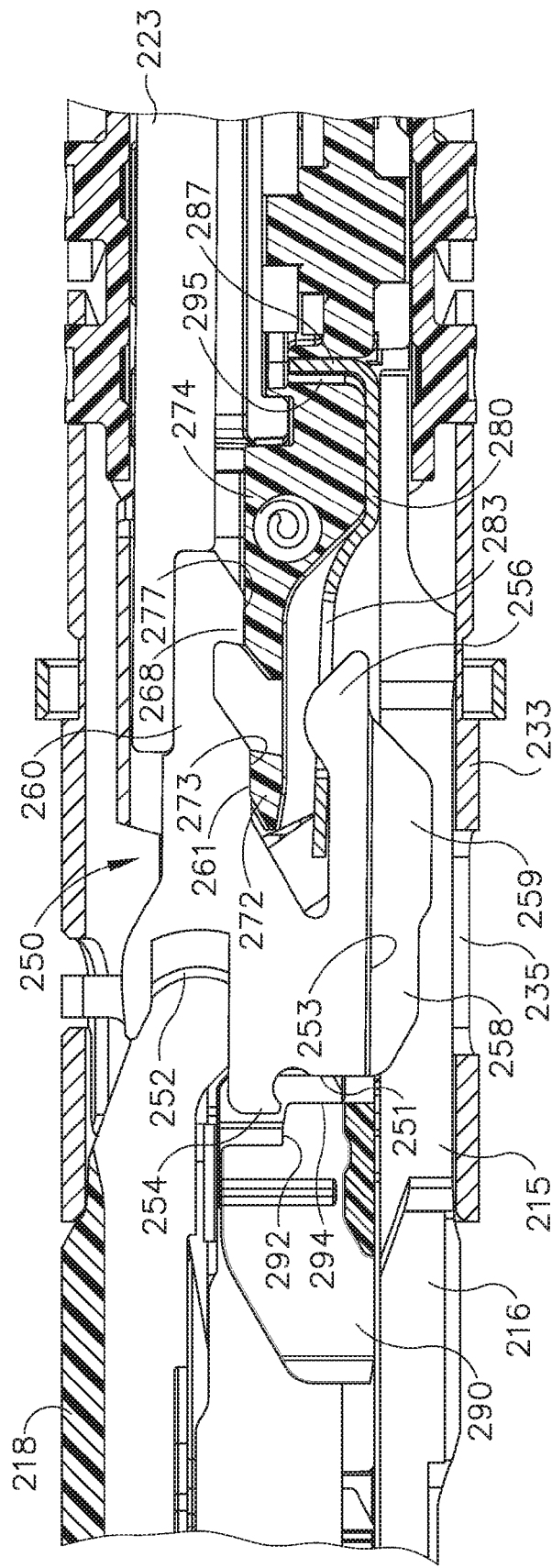
FIG. 25A depicts a side cross sectional view of the end effector of FIG. 13 in the initial position with a loaded cartridge.

FIG. 25A shows end effector (212) in an initial position just after jaws (216, 218) are closed with a properly loaded staple cartridge (237). In the initial position, upper extension (260) of blade assembly (250) is positioned above engagement features (272, 274) of frame member (270). Wall (261) of upper extension (260) is resting on wall (273) of first engagement feature (272), while tab (268) of upper extension (260) is resting on wall (277) of second engagement feature (274). Resilient member (280) is positioned between lower jaw (216) and frame member (270). Wall (287) of resilient member (280) is engaged with wall (295) of frame member (270) such that wall (295) is configured to axially retain resilient member (280). Opening (283) of resilient member is positioned above lower extension (255) of blade assembly (250) such that tab (256) of lower extension (255) is positioned within opening (283) of resilient member (280). Protrusion (258) of lower extension (255) is positioned within proximal portion (215) of slot (214) of lower jaw (216). Protrusion (258) is vertically aligned within slot (214) such that shelf (253) is positioned above slot (214). Distal tip (254) of blade assembly (250) is positioned above sled (290). Accordingly, blade assembly (250) is ready to be fired in from the initial position shown in FIG. 25A.

Figure 25B:
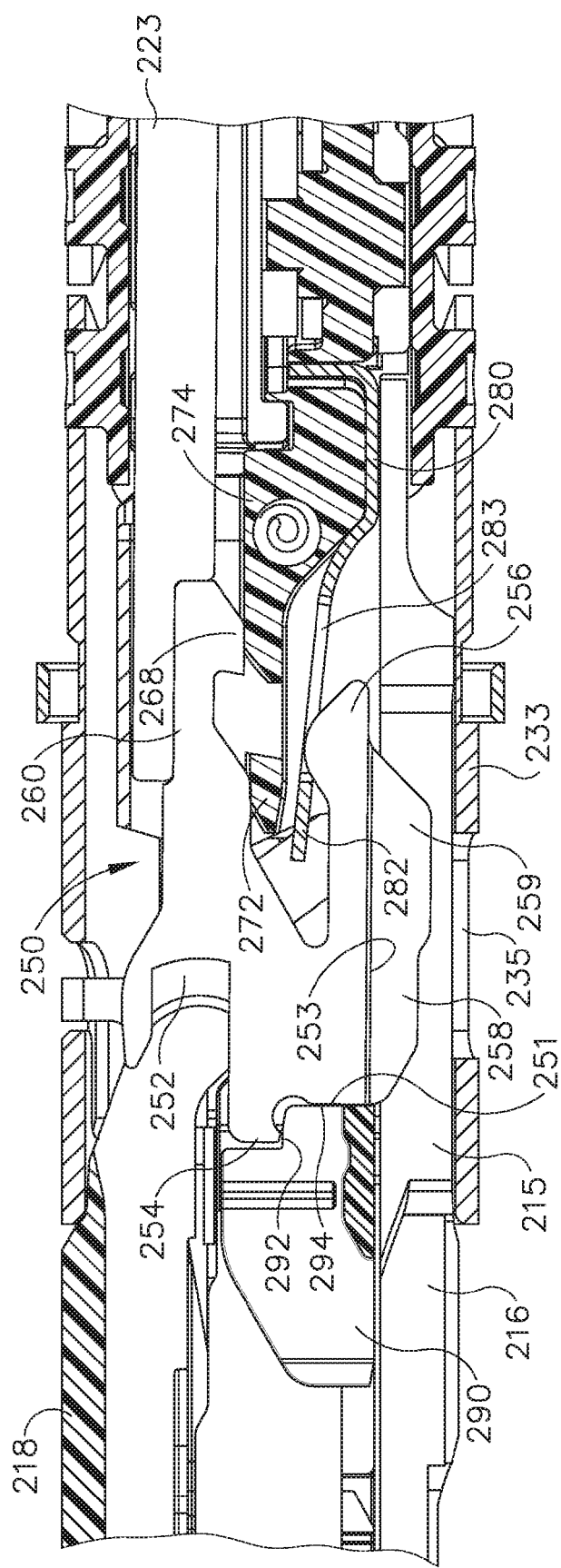
FIG. 25B depicts a side cross sectional view of the end effector of FIG. 13 in a first partially fired position with a loaded cartridge.
Figure 25C:
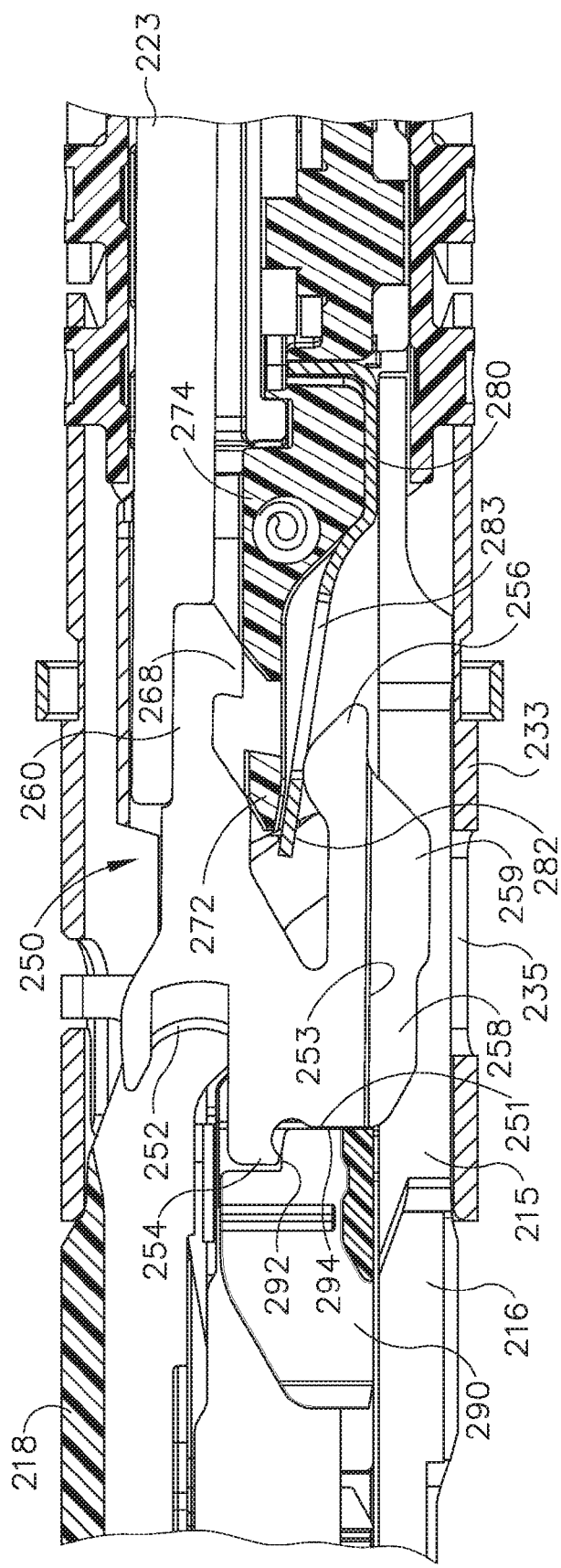
FIG. 25C depicts a side cross sectional view of the end effector of FIG. 13 in a second partially fired position with a loaded cartridge.
Figure 25D:
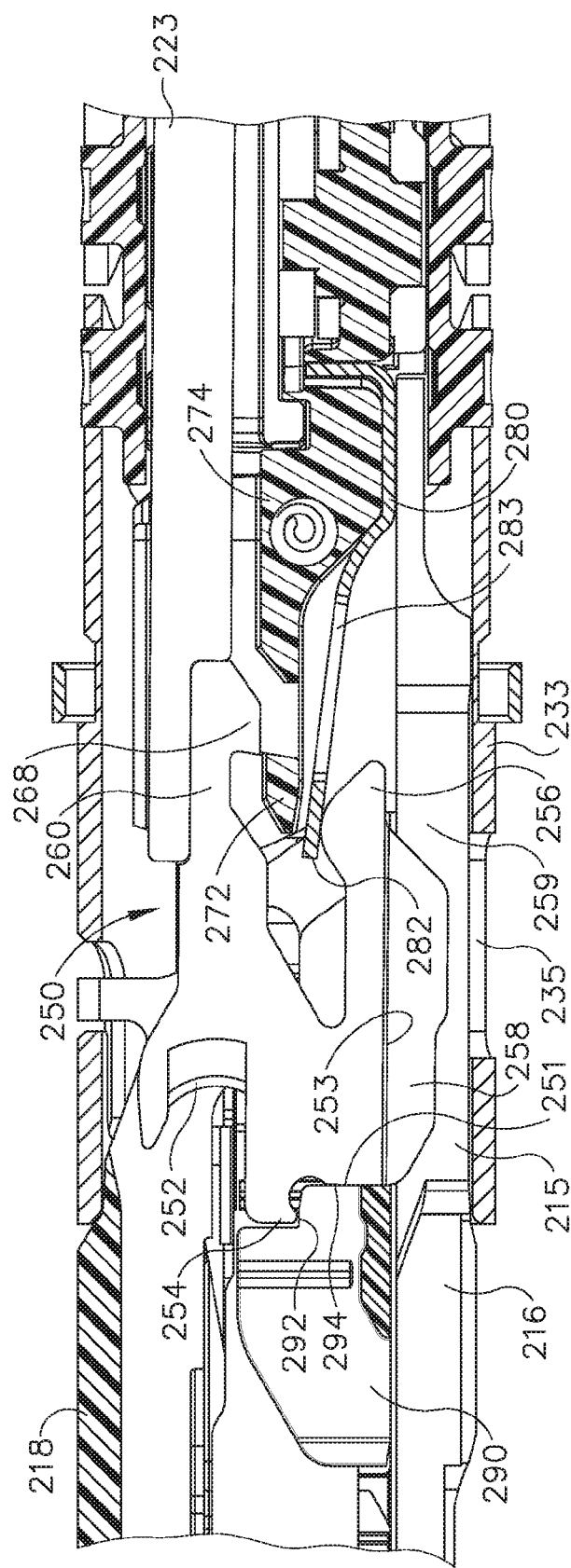
FIG. 25D depicts a side cross sectional view of the end effector of FIG. 13 in a third partially fired position with a loaded cartridge.
Figure 25E:
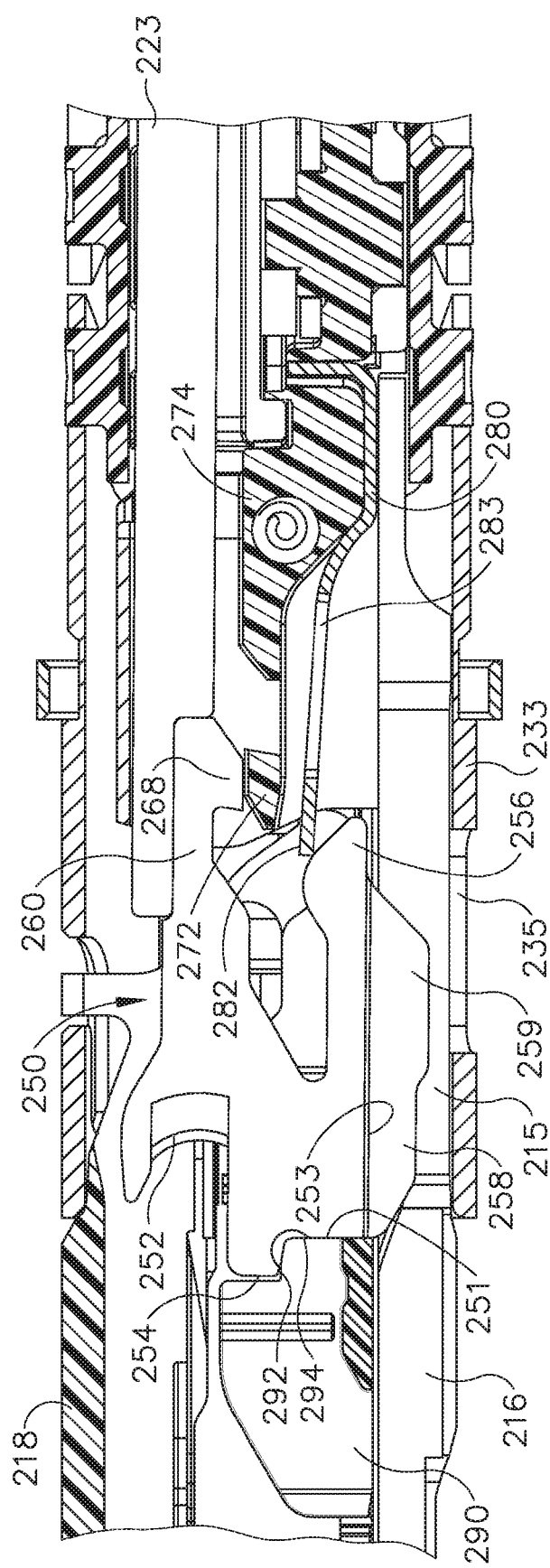
FIG. 25E depicts a side cross sectional view of the end effector of FIG. 13 in a fourth partially fired position with a loaded cartridge.
Figure 25F:
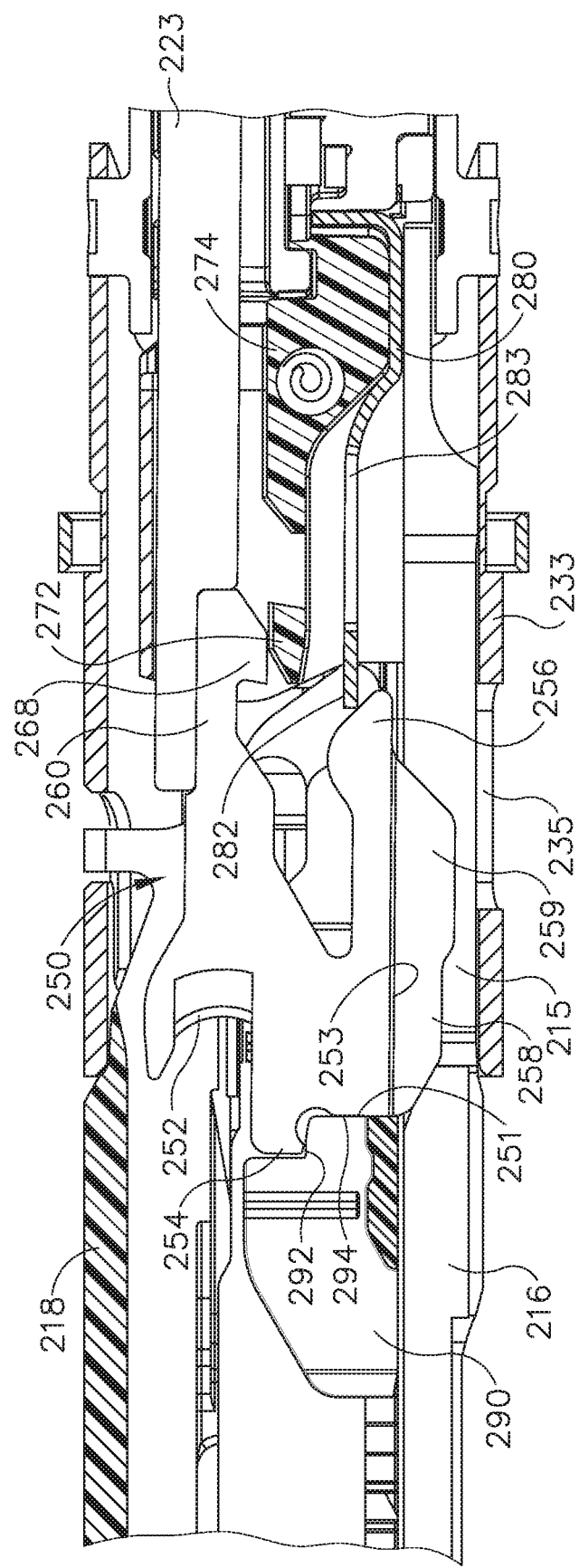
FIG. 25F depicts a side cross sectional view of the end effector of FIG. 13 in a fifth partially fired position with a loaded cartridge.

Firing trigger (28) may be actuated to drive firing beam (223) and blade assembly (250). As blade assembly (250) is driven distally, distal tip (254) of blade assembly (250) engages a top surface (292) of sled (290) and distal wall (251) of blade assembly (250) engages a proximal end (294) of sled (290), as shown in FIG. 25B. This maintains the vertical position of blade assembly (250) when blade assembly is positioned within proximal portion (215) of slot (214) of lower jaw (216). As blade assembly (250) travels further distally, tab (256) of blade assembly (250) travels distally from opening (283) of resilient member (280) such that tab (256) engages distal portion (282) of resilient member (280). Tab (256) thereby pushes distal portion (282) of resilient member (280) upwardly, as shown in FIG. 25C. Because sled (290) maintains the vertical position of blade assembly (250), tab (268) of blade assembly (250) translates distally above engagement features (272, 274) of frame member (270) such that tab (268) does not fall between engagement features (272, 274) to prevent the distal movement of blade assembly (250), as shown in FIG. 25D. Blade assembly (250) thus overrides the lockout position at this stage. Distal portion (282) of resilient member (280) then biases downwardly to a nominal position, proximal of tab (256) of blade assembly (250), as tab (256) translates distally from resilient member (280), as shown in FIG. 25E. Protrusion (258) of blade assembly (250) then enters distal portion (213) of slot (214) of lower jaw (216), as shown in FIG. 25F. Shelf (253) of blade assembly (250) is then positioned above slot (214) and tab (268) of upper extension (260) is above first engagement feature (272). Blade assembly (250) is then further translated distally to sever and staple tissue positioned between jaws (216, 218).

After blade assembly (250) is fired distally, blade assembly (250) may be retracted proximally within lower jaw (216). For example, blade assembly (250) may be retracted by beam (223) by automatic reversal of motor (102) upon detected completion of a firing stroke, in response to a second actuation of firing trigger (28), and/or otherwise. When blade assembly (250) is retracted, blade assembly (250) disengages from sled (290). Without sled (250), blade assembly (250) may fall downwardly to the lockout position of FIG. 23B as blade assembly (250) is retracted after being fired. Blade assembly (250) may be returned to the initial position of FIG. 23A after blade assembly (250) is in the lockout position of FIG. 23B, As blade assembly (250) is driven proximally by motor (102), ramped walls (262, 266) of upper extension (260) of blade assembly (250) slide proximally against ramped walls (271, 276) of engagement features (272, 274), As upper extension (260) translates proximally against engagement features (272, 274), walls (271, 276) of engagement features (272, 274) push upper extension (260) and blade assembly (250) upwardly through a camming action. Tab (256) of blade assembly (250) also travels upwardly to again be positioned within opening (283) of resilient member (280). This returns blade assembly (250) to the initial position, as shown in FIG. 23A.

Once tissue positioned between jaws (216, 218) is cut and stapled, end effector (2112) may be pivoted back to the nonarticulated position by articulation control (13) and removed from the surgical site, with jaws (216, 218) closed. Alternatively, jaws (216, 218) may be opened prior to pivoting end effector (212) to release any tissue between jaws (216, 218). Jaws (216, 218) may then be re-closed prior to removing end effector (212) from the surgical site. End effector (212) may then be opened to replace staple cartridge (237) with a new staple cartridge. To open end effector (212), closure trigger (26) may be released away from pistol grip (24). Staple cartridge (237) may be replaced with a new staple cartridge, and end effector (212) may be again inserted to the surgical site for further cutting and stapling.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instruments," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, now U.S. Pat. No. 8,479,969, issued Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, now U.S. Pat. No. 8,573,465, issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A stapling apparatus, comprising:
   (a) an end effector, wherein the end effector is operable to apply at least one staple at a surgical site;
   (b) a blade assembly operable to move between an unlocked position and a locked position, wherein the blade assembly is operable to move through the end effector in the unlocked position, wherein the blade assembly comprises:
      (i) a lockout engagement feature, and
      (ii) a resilient-member engagement feature, wherein the lockout engagement feature is proximal relative to the resilient-member engagement feature;
   (c) a lockout feature operable to engage the lockout engagement feature of the blade assembly to prevent the blade assembly from moving past a predetermined position when the blade assembly is in the locked position;
   (d) a resilient member configured to engage the resilient-member engagement feature of the blade assembly to bias the blade assembly toward the locked position; and
   (e) a staple cartridge assembly configured to fit in the end effector, wherein the staple cartridge assembly comprises a body and a sliding lockout bypass, wherein the sliding lockout bypass is configured to prevent the blade assembly from moving into the locked position such that the sliding lockout bypass is configured to enable the blade assembly to move past the predetermined position, wherein the sliding lockout bypass is configured to slide along at least part of a length of the body.

2. The stapling apparatus of claim 1, wherein the resilient member further defines a recess configured to house a portion of the blade assembly.

3. The stapling apparatus of claim 1, wherein the resilient-member engagement feature of the blade assembly further comprises a tab configured to engage the resilient member.

4. The stapling apparatus of claim 3, wherein the resilient member is configured to bias the tab such that the blade assembly is biased toward the locked position.

5. The stapling apparatus of claim 1, wherein the blade assembly is configured to drive the sliding lockout bypass to slide along at least part of the length of the body.

6. The stapling apparatus of claim 1, wherein the sliding lockout bypass comprises an engagement surface configured to receive a portion of the blade assembly to prevent the blade assembly from moving toward the locked position.

7. The stapling apparatus of claim 1, wherein the sliding lockout bypass further comprises a wedge sled configured to translate relative to the body to apply at least one staple.

8. The stapling apparatus of claim 1, wherein the lockout feature comprises a wall defining an opening configured to receive a portion of the lockout engagement feature of the blade assembly in the locked position.

9. The stapling apparatus of claim 1, further comprising a shaft assembly defining a longitudinal axis, wherein the end effector and lockout feature are configured to deflect relative to the longitudinal axis.

10. The stapling apparatus of claim 1, wherein the staple cartridge assembly further comprises a plurality of staples housed within the body.

11. The stapling apparatus of claim 10, wherein the body defines a plurality of staple apertures, wherein the sliding lockout bypass is configured to drive the plurality of staples through the plurality of staple apertures.

12. The stapling apparatus of claim 1, wherein the blade assembly further comprises a distal tip configured to engage the sliding lockout bypass.

13. The stapling apparatus of claim 12, wherein the blade assembly further comprises a cutting edge located proximally relative to the distal tip.

14. The stapling apparatus of claim 1, wherein the sliding lockout bypass is configured to translate with the blade assembly past the predetermined position.

15. A stapling apparatus, comprising:
   (a) an end effector, wherein the end effector is operable to apply at least one staple at a surgical site;
   (b) a blade assembly operable to translate through the end effector, wherein the blade assembly comprises:
      (i) a lockout engagement feature, and
      (ii) a resilient-member engagement feature, wherein the lockout engagement feature is proximal in relation to the resilient-member engagement feature;
   (c) a lockout feature configured to engage the lockout engagement feature to inhibit the blade assembly from translating through the end effector;
   (d) a resilient member configured to engage the resilient-member engagement feature to urge the blade assembly into engagement with the lockout feature; and
   (e) a staple cartridge configured to fit in the end effector, wherein the staple cartridge comprises:

(i) at least one staple; and (ii) a lockout bypass feature configured to prevent the lockout feature from inhibiting the blade assembly from translating through the end effector, wherein the lockout bypass feature is configured to translate through the end effector with the blade assembly.

16. The stapling apparatus of claim 15, wherein the blade assembly is operable to translate through a first range of motion in which the resilient member resiliently bears against the resilient-member engagement feature of the blade assembly, wherein the blade assembly is operable to translate through a second range of motion in which the resilient member does not resiliently bear against the resilient-member engagement feature of the blade assembly.

17. The stapling apparatus of claim 16, wherein a location of the second range of motion is proximal to a location of the first range of motion.

18. The stapling apparatus of claim 17, wherein the blade assembly is operable to translate through a third range of motion in which the resilient member does not resiliently bear against the blade assembly, wherein a location of the third range of motion is distal in relation to both the location of the first range of motion and the location of the second range of motion.

19. A stapling apparatus, comprising:

(a) an end effector, wherein the end effector is operable to apply at least one staple at a surgical site;

(b) a blade assembly operable to move through a first range of motion and a second range of motion through the end effector, wherein a location of the second range of motion is distal relative to a location of the first range of motion, wherein the blade assembly comprises:

(i) a lockout engagement feature, and (ii) a resilient-member engagement feature, wherein the lockout engagement feature is proximal relative to the resilient-member engagement feature;

(c) a lockout feature operable to engage the lockout engagement feature to prevent the blade assembly from moving from the first range of motion to the second range of motion;

(d) a resilient member operable to engage the resilient-member engagement feature to drive the lockout engagement feature toward the lockout feature; and (e) a staple cartridge assembly configured to fit in the end effector, wherein the staple cartridge assembly comprises a lockout bypass, wherein the lockout bypass is configured to engage the blade assembly during the first range of motion to bypass the lockout feature from preventing the blade assembly from traveling through the second range of motion, wherein the lockout bypass is configured to move with the blade assembly through the second range of motion.

\* \* \* \* \*